(12) United States Patent
McCue et al.

(10) Patent No.: US 7,439,419 B1
(45) Date of Patent: Oct. 21, 2008

(54) SOLANUM TUBEROSUM β-SOLANINE/β-CHACONINE RHAMNOSYL TRANSFERASE SEQUENCES AND USES THEREOF

(75) Inventors: Kent F. McCue, El Cerrito, CA (US); Paul V. Allen, Pinole, CA (US); David R. Rockhold, El Cerrito, CA (US); Louise V. T. Shepherd, Errol (GB); Mary M. Maccree, Woodland, CA (US); Howard V. Davies, Invergowrie (GB); William R. Belknap, Albany, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/272,958

(22) Filed: Nov. 14, 2005

(51) Int. Cl.
- *A01H 1/00* (2006.01)
- *C07H 21/04* (2006.01)
- *C07K 14/415* (2006.01)
- *C12N 15/29* (2006.01)

(52) U.S. Cl. .......................... 800/295; 435/6; 435/69.1; 435/468; 435/183; 435/419; 530/370; 536/23.2; 536/23.6; 800/278

(58) Field of Classification Search .................... 435/6, 435/69.1, 468, 419, 252.3, 320.1, 183; 530/370; 536/23.6; 800/278, 295
See application file for complete search history.

(56) References Cited

U.S. PATENT DOCUMENTS 5,959,180 A 9/1999 Moehs et al.

OTHER PUBLICATIONS

Muranaka et al. A_Geneseq_200701, Accession No. ADR70664, WO2004078979-A1, Sep. 16, 2004, SEQ ID No. 1.*
Bergenstrahle, A., E. Tillberg, and L. Jonsson, "Characterization of UDP-glucose:solanidine glucosyltransferase and UDP-galactose:solanidine galactosyltransferase from potato tuber," Plant Science (1992) 84:35-44.
Draper, J., and R. Scott, Chapter 4 "The Isolation of plant nucleic acids," In: Plant Genetic Transformation and Gene Expression—A Laboratory Manual, Eds: J. Draper, R. Scott, P. Armitage and R. Walden, (1998) Blackwell Scientific Publications pp. 199-236.
Esposito, F. et al., "Glycoalkaloid Content and Chemical Composition of Potatoes Improved with Nonconventional Breeding Approaches," J. Agric. Food Chem. (2002) 50:1553-1561.
McCue, K., et al., "The Primary in vivo steroidal alkaloid glucosyltransferase from potato," Phytochemistry (2006) In press.
McCue, K. et al., "Reduction of Total Steroidal Glycoalkaloids in Potato Tubers Using Antisense Constructs of a Gene Encoding a Solanidine Glucosyl Transferase," Acta Hort. (2003) 619:77-86.
McCue, K. et al., "Metobalic compensation of steroidal glycoalkaloid biosynthesis in transgenic potato tubers: using reverse genetics to confirm the in vivo enzyme function of a steroidal alkaloid galactosyltransferase," Plant Science (2005) 168:267-273.
Mensinga, T.T., et al., "Potato glycoalkaloids and adverse effects in humans: an ascending dose study," Regulatory Toxicology and Pharmacology (2005) 41:66-72.
Moehs, C.P., P. Allen, M. Friedman, and W.R. Belknap, "Cloning and expression of solanidine UDP-glucose glucosyltransferase from potato," The Plant Journal (1997) 11(2):227-236.
Paczkowski, C. and Z.A. Wojciechowski, "Glucosylation and Galactosylation of Diosgenin and Solasodine by Soluble Glycosyltransferase(s) from Solanum Melongena Leaves," Phytochemistry (1994) 35(6):1429-1434.
Stapleton, A., P.A. Allen, M. Friedman, and W.R. Belknap, "Purification and Characterization of Solanidine Glucosyltransferase from the Potato (*Solanum tuberosum*)," J. Agric. Food Chem. (1991) 39:1187-1193.
Valkonen, J.P.T., M. Keskitalo, T. Vasara and L. Pietila, "Potato Glycoalkaloids: A Burden or A Blessing?" Critical Reviews in Plant Sciences (1996) 15(1):1-20.
Van Der Leij, F.R., R.G.F. Visser, A.S. Ponstein, E. Jacobsen, and W.J. Feenstra, "Sequence of the structural gene for granule-bound starch synthase of potato (*Solanum tuberosum* L.) and evidence for a single point deletion in the amf allel," Mol. Gen. Genet. (1991) 228:240-248.
Zimowski, J., "Occurence of a Glycosyltransferase Specific for Solanidine in Potato Plants," Phytochemistry (1991) 30(6):1827-1831.

* cited by examiner

*Primary Examiner*—Phuong T Bui
(74) *Attorney, Agent, or Firm*—Elizabeth R. Sampson; Margaret A. Connor; Leslie Shaw

(57) ABSTRACT

Nucleic acid sequences from potato that encode the enzyme β-solanine/β-chaconine rhamnosyltransferase (SGT3) are disclosed. Recombinant DNA molecules containing the sequences, and use thereof, in particular, use of the sequences and antisense constructs to inhibit the production of SGT3 and thereby reduce levels of the predominant steroidal glycoalkaloids α-chaconine and α-solanine in Solanaceous plants such as potato are described.

10 Claims, 12 Drawing Sheets

```
Sgt3    ATGG---CGA-TGGAACAGAATGAAGAAACTGCAATGCCGCATGTTGTGTTCATACC-
Sgt1    ATGGTAGCAACCTGCAACAG-TGGCGA------AATCCTCCATGTTCTTTTCCTTCCCT
        ****    *  *  ** ***** **  **         *** *  ****** * *** *  **

Sgt3    ----ATACGCCATGACGAGTCATATAACTCCATTGGTACATATTGCTAGACTCTTCGCCC
Sgt1    TCTTATCCGC-TG----GTCATTTCATCCCATTAGTTAACGCCGCAAGGCTATTCGCCT
            ** ***  **       ***** * *  ***** **   *   ** **  ** ******

Sgt3    TCCATGGCCTCAAAGTTACTATCAT---TGCCCCTCAGCATAATGCTCTTCTTTTTCAGT
Sgt1    CCCGCGGTGTTAAAGCCACAATCCTCACTACCCCT---CATAATGCCTTACTTTTTAGAT
         **  **  * **** **  ** *      *  *****   ********  *  * ****** *

Sgt3    CCTCTGTCGATAGAGACCGTCTCTTTTCGGGCAGCAATATTACTGTCCGGACAATTCAAT
Sgt1    CTACTATTGACGATGATGTTCGAATTTCCGGATTTCCCATTTCTATCGTAACTATTAAAT
         *  **  * **     **    **   **** **    ***  ** **  ** ***  ***

Sgt3    TTCCGTCTGAGGAAGTTGGATTACCTGTAGGAATTGAAAACTTCATCGCAAGCCCTTCTA
Sgt1    TCCCCTCTGCTGAAGTTGGGTTGCCTGAAGGAATTGAGAGCTTTAACTCTGCCACTTCAC
         * ** ****   ********  **  **** ********* *  *** *  *  *  * ****

Sgt3    TGGAAATAGTTGGCAAAGTTCACTATGGGTTTATTCTGCTCCAAAAGATTATGGAGCAAC
Sgt1    CTGAAATGCCTCATAAAATTTTTATGCTCTTTCTCTTCTACAAAAGCCAATGGAAGATA
         *****   *   *** **     ****  **     **   *** ** ******     *****   *

Sgt3    TAATTCGGGAGATCAATCCAAACTGCATTGTTTCCGATATGTTCTTCCCTTGGACTGTTG
Sgt1    AAATTCGTGAACTCCGTCCTGATTGCATTTTTTCTGATATGTACTTCCCTTGGACAGTAG
         ****** **   ***   *  ****** **** ******* *********** ** *

Sgt3    ATTTAGCTGAGGAGATGCAAATTCCGAGATTTTCTTTTCAACCAGCCA-CTTCCAT----
Sgt1    ATATTGCTGATGAGCTTCACATCCCTCG-TATTTGTACAATTTGTCTGCTTACATGTGC
         ** * ***** ***  *  ** **  **    *  ** * *  ***    * *  *** ***

Sgt3    -ACATCAATGTGCTTGGGTTTTCATCAGGGAATTTAAACCTTACAAG------AATGTGG
Sgt1    TACAGCATTATGCA-----CAACCTTAAGGTTTACAGACCTCACAAGCAGCCTAATCTAG
          *** ** * ***  .      *  *  **   *  * **** *****        *** * *

Sgt3    CGTCGGATGCTGAAAAGTTTTTGATTCCTGGTTTGCCTCTCGACATCAAAATGAAAGTCT
Sgt1    A-CGAAT-CTCAAAGTTTCGTGGTTCCTGGTTTACCTGATGAGATAAAGTTCAAGTTAT
         ** ** **  ***  **  ** *********** ***   **  **  **  * *  *
```

FIG. 2A

```
Sgt3    CAGAGATTGA-AGATTTTCTTAAAGAGGAAACTGAGTACACAAAGACAGTAGATGACGTT
Sgt1    CCCA-ACTGACAGATGATCTGAGAAAGT---CGGATGACCAAAAGACTGTTTTTGACGAA
        *  *  * *** ****  *** *  * **       * **  ** ****** **   *****

Sgt3    TT------ACAAGCTGAGGTT---------CGTAGCCATGGTATTATTCATAACACTTGC
Sgt1    TTGCTCGAACAAGTTGAAGATTCGGAGGAACGAAGCTATGGCATTGTTCATGATACATTT
        **      ***** *** * *         ** *** **** *** ****** *  * *

Sgt3    TCTGAGCTGGAACCTGGC---GTTGCCCAACTCTACGAAAAAGCTAGAGGAGT-AAAAGG
Sgt1    TATGAGCTAGAACCTGCATATGTTGACTA---CTACCAGAAAT-AAAGAAACCAAAATG
        * ****** ******* *      ****  *    ****  *  ***  *  *    **** *

Sgt3    GTGGCATATAGGTCCACTTGCTCTGTTT--ATCAACAAATATGAAGC--GGAAATTAGTT
Sgt1    TTGGCATTTTGGTCCGCTCTCTCATTTTGCATCCA-AAATCCGTAGTAAGGAACTAATTT
        ****** * ***** **  **  ***     ***  ****      *  **** *  * **

Sgt3    CTAAACAAATTTCCAATTCGAATATTAATTCATGTTCTGACCCTTGGAAAGGGTACGGTG
Sgt1    CTGAGCATAACAACAATGAGATTGTTA-------------------------TA----G
        ** * **  *    ****  ** *  * ***                           **    *

Sgt3    ATTGTTTCAATTGGCTTGAAAATCAACAACCTAACTCCGTTCTCTTTGTTTGCTTTGGAA
Sgt1    ATTGGTTGAAT--GCA-------CAGAAACCTAAATCGGTTCTCTATGTATCTTTCGGAA
        **** ** ***  **        ** ******* ** ******* *** *  *** ****

Sgt3    GCATGATAAGATTTTCCGATGATCAGCTTAAGGAAATGGCTGTTGGATTGAAGGCTGCCA
Sgt1    GCATGGCTAGATTTCCTGAGAGCCAACTGAATGAAATAGCCCAAGCTCTGGATGCTTCAA
        *****     ****** * **   ** ** ** ***** **  *       *  * *** * *

Sgt3    ACTGTCCAACTATTTGGGTTTTTAGGGAGCAGGACAAAAATGAAGTAGACGAGAAAGATG
Sgt1    ATGTTCCTTTCATTTTTGTATTGAGGC--C-------TAATGAAG-AAACG---------
         *  ***    ****  ** ** ***   *            ******* *  ***

Sgt3    AGCATTCTGACTGG-AGCCG-TAATGGTTTCAAAGAAATGATTGGGGAAAGATGTTTAT
Sgt1    -GCGTCGTGGTTGCCAGTTGGTAAT--TTAG-AGGACAAGACT----AAAAAGGGTTTGT
         ** *  **  **  **  **  ****   * ** * **  *          ****   **** *

Sgt3    -CATCCAAGGCTGGGCACCACAACAATTA--ATCCTGAAACATCAAGCAATTGGTGGATT
Sgt1    ACATCAAAGGGTGGGTCCCACAGC--TTACGATCATGGAACATTCAGCAACAGGCGGGTT
         **** **** ****  ***** *   * **   *** ** ** ****** ****  ** ** **
```

FIG. 2B

```
Sgt3   CTTAACTCATTGTGGTTGGAACTCTATACTTGAGTCTCTAGCCGTAGGTGTTCCATTGAT
Sgt1   CATGACTCATTGTGGTACTAATTCGGTTCTGGAAGCCATCACTTTTGGCGTGCCAATGAT
       *  * ***********   **  **  *  ** **    *   *    * ** ** *** ****

Sgt3   CACATGGCCACTTTTCTCAGACAACTTCTATACCGACAAGCTTTTGGAGACACTTGGCCT
Sgt1   AACATGGCCACTTTATGCTGATCAATTCTACAACGAGAAGGTAGTCGAGGTTAGGGGATT
        ************   *  **   * ***** *  *** ***  *  *  * ***      ** *

Sgt3   TGCTATTGGAATTGGAGCAGATGTGTGGAATCCGGGGTTT-ATATTATCGTGTCCACCCC
Sgt1   GGGAATCAAAATCGGGATAGATGTATGGAATGAAGGGATTGAGATCA-CGGG-----CCC
         *  **    ***  **   ****** ******    *** **  * **  * ** *         ***

Sgt3   TTTCAG-GAGAG----AAGAT-AGAGTTGGCCGTCAAGCGTTTAATGA------ATAATT
Sgt1   TGTAATAGAAAGCGCCAAGATTAGAGAAG-CAATTGAGAGACTAATGATCAGTAATGGTT
       * * *   ** **      ***** ****    *     *  ** *     ******     **   **

Sgt3   CAGAGGAAAGTAGAAAAATTAGAGAAAATGCAAAGTTGATG-GCAAAGAAGCTCAAAAGT
Sgt1   CTGAGGAAATTATAAATATTAGGGATAGAGTAATGGCTATGAGCAAAATGGCTCAGAA-T
       * ******* **  *** ***** **  *    * **  *   *** ***** *****  ** *

Sgt3   GCCACTGAAGAAGGTGGTTCCTCT-----CATTCACAGCTTATCGGGTTAATTGAGGAGA
Sgt1   GCAACAAATGAAGGTGGATCTTCGTGGAACAATCTCA-CTGCTC----TCATTCAACATA
       ** **  * ********  ** **       ** **  ** **   **       *  *** *  * *

Sgt3   TCAAGCGTTGTGCTTTCAAGAAATCCTTTTAG
Sgt1   TCAAGAATTATAATCTTAA--------T-TAG
       *****  ** *  *  * **         * ***
```

FIG. 2C

```
SGT3    MAMEQNEETAMPHVVFIPYAMTSHITPLVHIARLFALHGLKVTIIAPQHNALLFQSSVDR
SGT1    MVATCNS-GEILHVLFLPFLSAGHFIPLVNAARLFASRGVKATILTTPHNALLFRSTIDD
        *.    *.   : **:*:*:    :.*: ***:  *****  :*:*.**::.  ******:*::*

SGT3    DRLFSGSNITVRTIQFPSEEVGLPVGIENFIASPSMEIVGKVHYGFILLQKIMEQLIREI
SGT1    DVRISGFPISIVTIKFPSAEVGLPEGIESFNSATSPEMPHKIFYALSLLQKPMEDKIREL
        *  :**  *:: **:*** ***** ***.*  ::.* *:    *:.*.: **** **: ***:

SGT3    NPNCIVSDMFFPWTVDLAEEMQIPRFSFQPATSIHQCAWVF--IREFKPYKNVASD-AEK
SGT1    RPDCIFSDMYFPWTVDIADELHIPRILYN--LSAYMCYSIMHNLKVYRPHKQPNLDESQS
        .*:**.***:******:*:*::***:  ::   *.: *   ::   ::  ::*:*:    *  ::.

SGT3    FLIPGLPLDIKMKVSEIEDFLKEETEYTKTVDDVLQ----AEVRSHGIIHNTCSELEPGV
SGT1    FVVPGLPDEIKFKLSQLTDDLRKSDDQKTVFDELLEQVEDSEERSYGIVHDTFYELEPAY
        *::****  :**:*:*::  *  *:::.   :  ....*::*:        :*  **:**:*:* ****.

SGT3    AQLYEKARGVKGWHIGPLALFINKYEAEISSKQISNSNINSCSDPWKGYGDCFNWLENQQ
SGT1    VDYYQKLKKPKCWHFGPLSHFASKIR---SKELISEHNNN------EIVID---WLNAQK
        .: *:*  :  * **:***:  *.*  .   *.:  **:  * *         :    *     **:  *:

SGT3    PNSVLFVCFGSMIRFSDDQLKEMAVGLKAANCPTIWVFREQDKNEVDEKDEHSDWSRNGF
SGT1    PKSVLYVSFGSMARFPESQLNEIAQALDASNVPFIFVLRP---NE-----ETASWLPVGN
        *:***:*.****  **.::**:*:*  .*.*:*  * *:*:*        **       *  :.*     *

SGT3    KEMIGEKMFIIQGWAPQQLILKHQAIGGFLTHCGWNSILESLAVGVPLITWPLFSDNFYT
SGT1    LEDKTKKGLYIKGWVPQLTIMEHSATGGFMTHCGTNSVLEAITFGVPMITWPLYADQFYN
        *     :*  : *:**.**   *::.*.* ***:****  **:**:::.***:*****::*:**.

SGT3    DKLLETLGLAIGIGADVWNPGFILSCPPLSGEKIELAVKRLMN-N-SEESRKIRENAKLM
SGT1    EKVVEVRGLGIKIGIDVWNEGIEITGPVIESAKIREAIERLMISNGSEEIINIRDRVMAM
        :*::*. **.* ** **** *: :: * :..  **. *::*** * ***  :**:..   *

SGT3    AKKLKSATEEGGSSHSQLIGLIEEIKRCAFKKSS
SGT1    SKMAQNATNEGGSSWNNLTALIQHIK--NYNLN-
        :*   :.**:***** .:* .**:.**   :: .
```

FIG. 3

SOLANUM TUBEROSUM β-SOLANINE/β-CHACONINE RHAMNOSYL TRANSFERASE SEQUENCES AND USES THEREOF

CROSS REFERENCE TO RELATED APPLICATION

This application is related to commonly assigned application Ser. No. 11/272,952, filed concurrently herewith, by Kent F. McCue, Paul V. Allen, David R. Rockhold, Louise V. T. Shepherd, Mary M. Maccree, Howard V. Davies, and William R. Belknap, entitled, "*Solanum Tuberosum* Sterol Alkaloid Glycosyltransferase (Sgt) A Novel Solanidine Glucosyltransferase Sgt2 and Uses Thereof," herein incorporated by reference in its entirety.

BACKGROUND OF THE INVENTION

1. Field of the Invention

The present invention is directed to the steroidal alkaloid glycosyl transferase enzyme β-solanine/β-chaconine rhamnosyltransferase (SGT3) which is involved in the biosynthesis of steroidal glycoalkaloids in Solanaceous plants. More particularly, the invention is directed to nucleic acid sequences that encode SGT3, recombinant polynucleotide molecules containing the sequences, and uses thereof. A particular use of the nucleic acid sequences and portions thereof is to inhibit SGT3 activity and reduce the levels of the steroidal glycoalkaloids α-chaconine and α-solanine in Solanaceous plants.

2. Description of the Art

Solanaceous plants include such agronomically important crops as potato, tomato and eggplant. Many Solanaceous species, including potato, synthesize bitter tasting steroidal glycoalkaloids (nitrogen-containing steroidal glycosides) as a defense against microbial or insect pests or in response to environmental stress. Accumulation of these natural toxicants can affect food quality and safety, especially in improperly stored or processed potatoes. This has led to the implementation of a guidelines limiting glycoalkaloid content in a tuber of a given potato cultivar to 20 mg/100 gm. While the guidelines provide effective protection for the consumer, its effectiveness is dependent upon limiting the release of new cultivars for commercial production to those with acceptable glycoalkaloid levels. For potato breeding programs to develop new cultivars with improved agronomic or processing properties, the need to select also for low levels of glycoalkaloids can present a difficult problem. A method to decrease the glycoalkaloid content of any newly developed cultivar with minimum impact on other characteristics would be of great use to obtain valuable new commercial potato cultivars.

SUMMARY OF THE INVENTION

The present invention is directed to the steroidal alkaloid glycosyl transferase enzyme β-solanine/β-chaconine rhamnosyltransferase (SGT3) that is involved in the biosynthesis of steroidal glycoalkaloids in Solanaceous plants. More particularly, the invention is directed to nucleic acid sequences that encode SGT3, recombinant polynucleotide molecules containing the sequences, and uses thereof. A particular use of the nucleic acid sequences and portions thereof is to inhibit SGT3 activity and reduce the levels of the steroidal glycoalkaloids α-chaconine and α-solanine in Solanaceous plants.

In cultivated potato the predominant glycoalkaloid species, α-chaconine and α-solanine, are triglycosylated derivatives of the aglycone solanidine. These steroidal glycoalkaloids contain either glucose (α-chaconine) or galactose (α-solanine) as the primary glycosyl residue. A proposed steroidal glycoalkaloid biosynthetic pathway illustrating biosynthesis of the glycoalkaloids α-chaconine and α-solanine is shown in FIG. 1. The final step in the synthesis of α-chaconine and α-solanine is catalyzed by SGT3. As discussed in detail herein, the present invention finds particular use to inhibit SGT3 activity and reduce the levels of the steroidal glycoalkaloids α-chaconine and α-solanine in Solanaceous plants.

In one aspect, the present invention is directed to isolated nucleic acid molecules that encode a polypeptide having SGT3 activity. The Sgt3 gene sequence is specifically exemplified herein (SEQ ID NO: 1). The deduced amino acid sequence is shown in SEQ ID NO:2.

Nucleic acid sequences having at least 99% sequence identity with the exemplified Sgt3 sequence as described in detail, below, and which encode a polypeptide having SGT3 activity are also encompassed by the present invention.

Nucleic acid sequences which hybridize specifically to the SGT3 coding sequence or its complement under high stringency conditions and which encode a polypeptide having SGT3 activity are also encompassed by the present invention.

The invention is also directed to recombinant nucleic acid molecules, the RNA equivalent, the complement of the DNA molecules, and vectors such as cloning, expression or transformation vectors comprising the nucleic acid sequences or molecules.

The invention is also directed to host cells comprising the nucleic acid sequences. The sequences may be used to encode an SGT3 polypeptide or for gene silencing methods. Such gene silencing methods include providing cells transformed with multiple copies of the sequence in the sense orientation for gene silencing, transforming the plants or plant cells with an antisense nucleotide sequence complementary to an mRNA-encoding SGT3 or other gene silencing methods as known in the art.

In particular, the invention is directed to plants or plant cells transformed with the sequences or constructs containing the sequences or fragments thereof to provide plants having reduced levels of glycoalkaloids. Such plants include, for example, Solanaceous plants. Prominent food crops are in the Solanaceae family. These include potato (*Solanum tuberosum*); tomato (*Lysopersicon*, e.g., *L. lycopersicum* and *L. esculentum*); pepper (*Capsicum*); eggplant (*Solanum melongena*). Most preferably, in the practice of the invention, the Solanaceous plant is potato.

Use of construction of antisense constructs containing a partial Sgt3 sequence to alter glycoalkaloid biosynthesis is encompassed by the invention. This is described in detail in the Example, below.

The present invention is also directed to isolated polypeptides having SGT3 activity. SEQ ID NO:2 shows the amino acid sequence encoded by the exemplified DNA sequence SEQ ID NO:1. A polypeptide having an amino acid sequence which has at least 99% sequence identity with the exemplified sequence SEQ ID NO:2, as described in detail, below, is encompassed by the invention. Polypeptide encoded by a nucleic acid sequence which hybridizes under high stringency conditions with the exemplified Sgt3 nucleic acid sequence as discussed in detail, below, are also encompassed by the invention. Variants of the polypeptides are encompassed by the invention as well as fragments having SGT3 activity. The activity and kinetics of the enzyme SGT3 have not been demonstrated in vitro prior to our invention and are demonstrated for the first time here using reverse genetics in transgenic plants.

Another aspect of the invention is the provision of methods of use of the sequences and enzyme. Such methods include use as probes capable of detecting the Sgt3 gene or fragment thereof, methods to obtain purified SGT3, methods for reducing steroidal glycoalkaloids in plants, methods for increasing steroidal glycoalkaloids in plants by increasing expression of SGT3, such as by increasing the copy number of the gene.

SEQ ID NO:3 shows a SGT3 partial sequence that was used for construction of antisense constructs for the transgenic plant lines. This is described in detail in the Example below.

The invention represents the first cloning and demonstration of the function of the gene encoding SGT3. One of the primary advantages of the invention is that it can provide a method to reduce toxic glycoalkaloid concentrations in Solanaceous species. Such a method offers a wide variety of benefits extending from the farm, to processing, shipping, and finally to marketing of potatoes and potato products. The ability to reduce toxicant levels in selected varieties will allow introduction of new potato cultivars that cannot currently be released due to glycoalkaloid concentrations exceeding the acceptable level. The utilization of direct genetic modification is especially important to avoid problems of classic potato breeding programs. The genome of commercial potato cultivars grown in the United States (which are tetraploid and highly heterozygous) is exceedingly complex. This genetic complexity makes it essentially impossible for breeders to introduce a single genetic trait into an existing cultivar, while maintaining its original properties. The invention provides a means to insert a sense or antisense Sgt3 transgene into the genome of these cultivars without altering the existing genes.

Another advantage of the invention is that it provides a means of solving problems in potato storage and shipping due to glycoalkaloids. Inappropriate post-harvest handling of tubers can result in increased glycoalkaloid biosynthesis in current commercial cultivars. The modification of glycoalkaloid biosynthetic pathways is beneficial to reduce or eliminate glycoalkaloid biosynthesis during storage and shipping.

Other objects and advantages of this invention will become readily apparent from the ensuing description.

BRIEF DESCRIPTION OF THE DRAWINGS

FIGS. 2A, B and C shows the alignment of Sgt3 (SEQ ID NO:16) and Sgt1 (SEQ ID NO:18) nucleotide sequences showing regions of identity and similarity.

FIG. 3 shows the alignment of SGT3 (SEQ ID NO:2) and SGT1 (SEQ ID NO:19) deduced amino acid sequences showing regions of identity and similarity.

BRIEF DESCRIPTION OF THE SEQUENCES

Figure 1:
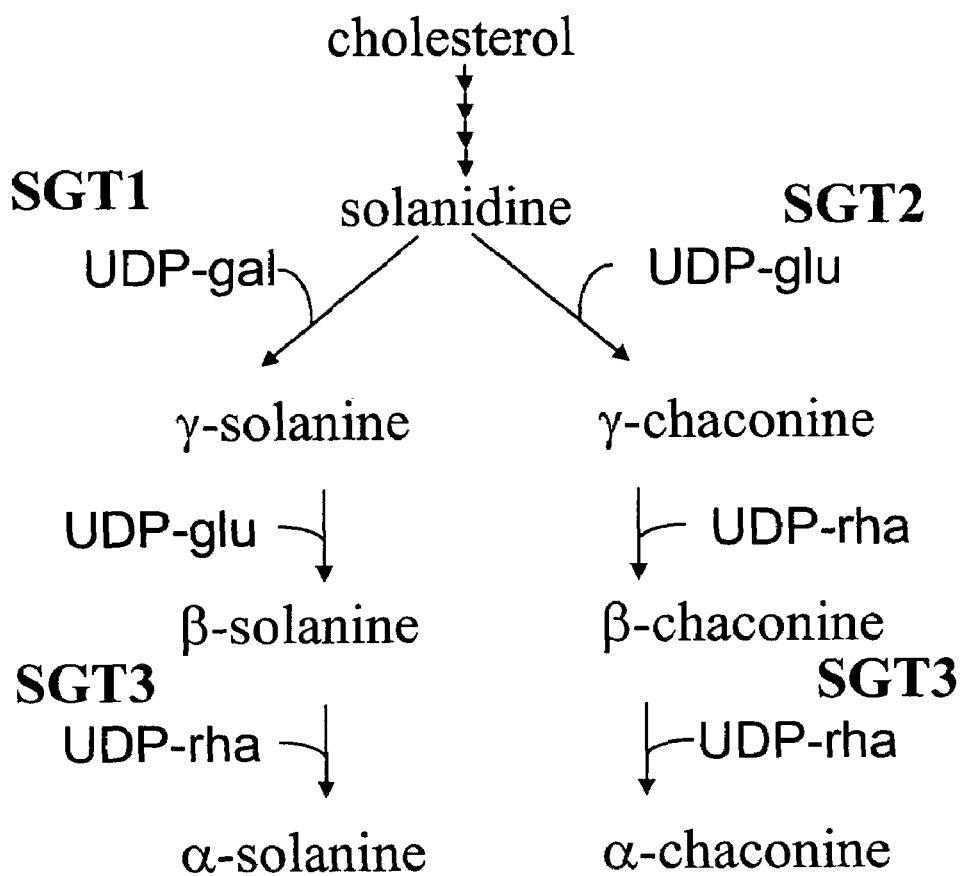
FIG. 1 shows the proposed SGA biosynthetic pathway for synthesis of α-solanine and α-chaconine, the two predominant potato steroidal glycoalkaloids from the aglycone, solanidine.

SEQ ID NO:1 shows the cDNA sequence of the *Solanum tuberosum* Sgt3 gene. Sequence feature information: *Solanum tuberosum* Sgt3 cDNA sequence: nucleotide 1 to 1671; coding region: nucleotide 7 to 1521, translation initiation codon: nucleotide 7 to 9; translation termination codon: nucleotide 1522 to 1524.

SEQ ID NO:2 shows the amino acid sequence encoded by SEQ ID NO:1.

SEQ ID NO:3 shows a SGT3 partial sequence that was used for construction of antisense constructs for the transgenic plant lines. This is described in detail in the Example below.

SEQ ID NO:4 is primer WRB 1439—Forward.

SEQ ID NO:5 is primer WRB 1440—Reverse.

SEQ ID NO:6 is primer WRB 1538 SGT3 R326— Sgt3 5-prime Reverse.

SEQ ID NO:7 is primer WRB 1535 SGT3 F820—Sgt3 3-prime Forward.

SEQ ID NO:8 is primer WRB 1526 PCR gt11 Rev—M13 Reverse Vector.

SEQ ID NO:9 is primer WRB 1620—Sgt3 5' KpnI Kozak.

SEQ ID NO:10 is primer WRB 1621—Sgt3 3' KpnI native stop.

SEQ ID NO:11 is primer WRB 1624—Sgt3 3' XhoI read through fusion.

SEQ ID NO:12 shows the coding sequence of the *Solanum tuberosum* Sgt3K9 native protein expression fragment. Sequence feature information: *Solanum tuberosum* Sgt3 cDNA fragment: nucleotide 1 to 1529; KpnI restriction endonucleases recognition site: nucleotide 1 to 6; translation initiation codon: nucleotide 7 to 9; coding region: nucleotide 7 to 1521; synthetic translation termination codon: nucleotide 1522 to 1524; KpnI restriction endonucleases recognition site: nucleotide 1524 to 1529.

SEQ ID NO:13 shows the amino acid sequence encoded by SEQ ID NO:12. The Sgt3K9 translated protein has a single E->K at position 502 compared to SEQ ID: NO2.

SEQ ID NO:14 shows the coding sequence of the *Solanum tuberosum* Sgt3KX9 fusion protein expression fragment. Sequence feature information: *Solanum tuberosum* Sgt3 cDNA fragment: nucleotide 1 to 1527; KpnI restriction endonucleases recognition site: nucleotide 1 to 6; coding region: nucleotide 7 to 1521; translation initiation codon: nucleotide 7 to 9; XhoI restriction endonucleases recognition site: nucleotide 1522 to 1527. Sgt3KX9 cDNA from 7 to 1521 is 100% identical to SEQ ID NO:1.

SEQ ID NO:15 shows the amino acid sequence encoded by SEQ ID NO:14.

SEQ ID NO:16 shows the cDNA sequence of the *Solanum tuberosum* Sgt3 gene without the first 6 and last 5 nucleotides of the flanking KpnI restriction endonuclease recognition sites shown in SEQ ID NO:12.

SEQ ID NO:17 shows the amino acid sequence encoded by SEQ ID NO:16.

SEQ ID NO:18 shows the cDNA sequence of the *Solanum tuberosum* Sgt1 gene.

SEQ ID NO:19 shows the amino acid sequence of SGT1 encoded by SEQ ID NO:18.

Incorporation-by-Reference of Material Submitted on a Compact Disc

Incorporated herein by reference in its entirety is a Sequence Listing, including SEQ ID NO:1 through SEQ ID NO:19. The Sequence Listing is contained on a diskette (3.5 in.), two identical copies of which are filed herewith. The Sequence Listing, in IBM/PC MS-DOS format (named "McCue 01 1803.txt"), PatentIn Version 3.3, was recorded on Nov. 9, 2005, and is 60 kilobytes in size.

Deposit of Biological Material (Plasmids Containing Sequences)

*Escherichia coli* strain pYES2.1 Sgt3 CDS KX9, containing the Sgt3 KX9 clone described herein was deposited on Nov. 4, 2005, under the provisions of the Budapest Treaty in the Agricultural Research Culture Collection (NRRL) in Peoria, Ill., and has been assigned Accession No. NRRL B-30885. Plasmid pYES2.1 Sgt3 CDS KX9 contains a sequence corresponding to SEQ ID NO:14.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton, et al., Dictionary of Microbiology and Molecular Biology (2d ed. 1994); The Cambridge Dictionary of Science and Technology (Walker ed., 1988); The Glossary of Genetics, 5th Ed., Rieger, R., et al. (eds.), Springer Verlag (1991); and Hale & Marham, The Harper Collins Dictionary of Biology (1991). References providing standard molecular biological procedures include Sambrook et al. (1989) *Molecular Cloning*, second edition, Cold Spring Harbor Laboratory, Plainview, N.Y.; *DNA Cloning*, Vols. I and II, IRL Press, Oxford, UK; and Hames and Higgins (eds.) (1985) Nucleic Acid Hybridization, IRL Press, Oxford, UK. References related to the manipulation and transformation of plant tissue include Kung and Arntzen (eds.) (1989) *Plant Biotechnology*, Butterworths, Stoneham, Mass.; R. A. Dixon (ed.) (1985) *Plant Cell Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) Academic Press, San Diego, Calif.; I. Potrykus (1991) *Ann. Rev. Plant Physiol. Plant Mol. Biol.* 42:205; Weising et al. (1988) *Annu. Rev. Genet.* 22:421; van Wordragen et al. (1992) *Plant Mol. Biol. Rep.* 19:12; Davey et al. (1989) *Plant Mol. Biol.* 13:273; Walden and Schell (1990) *Eur. J. Biochem.* 192:563; Joersbo and Brunstedt (1991) *Physiol. Plant.* 81:256 and references cited in those references. The references cited in the list of References attached below also provide a description of the terms used herein. The following U.S. patents are incorporated herein by reference: U.S. Pat. Nos. 5,959,180, 6,084,156, 6,940,003, and 5,231,020. All references cited in the present application are expressly incorporated by reference herein.

To facilitate understanding of the invention, a number of terms are defined below.

The polypeptide encoded by the Sgt3 gene is the enzyme β-solanine/β-chaconine rhamnosyl transferase, denoted herein as SGT3. As shown in FIG. 1, this enzyme catalyzes the final step in the synthesis of α-chaconine and α-solanine, is catalyzed by SGT3. The enzyme carries out the rhamnose dependent conversion of the diglycosyl steroidal alkaloids β-solanine and β-chaconine to α-solanine and α-chaconine, respectively.

As defined herein, "SGT3" includes all enzymes that are capable of catalyzing the rhamnose dependent conversion of the diglycosyl steroidal alkaloids β-solanine and β-chaconine to α-solanine and α-chaconine, respectively. The amino acid sequence of the enzyme may or may not be identical with the amino acid sequence that occurs naturally in Solanaceous plants. In addition, artificially induced mutations are also included so long as they do not destroy activity. The definition of SGT3 used herein includes these variants that are derived by direct or indirect manipulation of the disclosed sequences.

It is also understood that the primary structure may be altered by post-translational processing or by subsequent chemical manipulation to result in a derivatized protein which contains, for example, glycosylated residues, oxidized forms of, for example, cysteine or proline, conjugation to additional moieties, such as carriers, solid supports, and the like.

These alterations do not remove the protein from the definition of SGT3 so long as its capacity to catalyze the rhamnose dependent conversion of the β-glycosterols to α-solanine and β-chaconine is maintained.

Thus, the identity of an enzyme as "SGT3" can be confirmed by its ability to inhibit or prevent the accumulation of both α-solanine and α-chaconine with the resulting partial buildup of β-solanine, γ-solanine, β-chaconine, and γ-chaconine when introduced in an antisense construct into potatoes.

While alternative forms of assessment of SGT can be devised, and variations on the above protocol are certainly permissible, the foregoing provides a definite criterion for the establishment of SGT3 activity and classification of a test protein as SGT3.

Preferred forms of SGT3 of the invention include those illustrated herein and those derivable by systematic mutation of the genes. Such systematic mutation may be desirable to enhance the SGT3 properties of the enzyme, to enhance the characteristics of the enzyme which are ancillary to its activity, such as stability, or shelf life, or may be desirable to provide inactive forms useful in the control of SGT3 activity in vivo, as further described below.

The β-solanine/β-chaconine rhamnosyltransferase gene, denoted herein as Sgt3, can also be described as SOLtu:Sgt3, a member of the *Solanum tuberosum* sterolalkaloid glycosyl transferase gene family encoding the SGT3 enzyme, β-solanine/β-chaconine rhamnosyltransferase. The coding sequence is shown in SEQ ID NO:1 from nucleotide 7 to 1521.

Sgt3 coding sequences include all sequences in purified and isolated form that encode a polypeptide having SGT3 activity as defined above. The term "coding sequence" is defined herein as a nucleic acid sequence which directly specifies the amino acid sequence of its protein product, e.g., a sequence which is transcribed into mRNA and translated into a polypeptide. The boundaries of the coding sequence are generally determined by the ATG start codon (eukaryotes) and a translation terminator (stop codon). A coding sequence can include, but is not limited to, DNA, RNA, cDNA, and recombinant nucleic acid sequences.

Nucleic acid sequences having at least 99% sequence identity with SEQ ID NO:1 from nucleotide 7 to nucleotide 1521 and having SGT3 activity are also encompassed by the present invention.

The term "identity," as known in the art, is a relationship between two or more polypeptide sequences or two or more polynucleotide sequences, as determined by a comparison of the sequences. In the art, "identity" also means the degree of sequence relatedness between polypeptide or polynucleotide sequences, as determined by the match between strings of such sequences. "Identity" can be readily calculated by known methods, including but not limited to those described in Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; and Sequence Analysis in Molecular Biology, von Heinje, G., Academic Press, 1987. Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990) and Altschul et al., Gapped BLAST and PSI-BLAST: a new generation of protein database search programs. Nucleic Acids Res. 25: 3389-3402 (1997).), ALIGN and ClustalW [Higgens, D. G. et al., 1989, Comput. Appl. Biosci, 5(2), 151-3].

"Percentage of sequence identity" is determined by comparing two optimally aligned sequences over a comparison window, wherein the portion of the polynucleotide sequence or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. It is preferred that the comparison window is at least 50% of the coding sequence, preferably 60%, more preferably 75% or 85%, and even more preferably 95% to 100%.

Nucleic acid sequences which hybridize specifically to the SGT3 coding sequence or its complement under high stringency conditions and which encode a polypeptide having SGT3 activity are also encompassed by the present invention. These include DNA sequences that hybridize specifically to a Sgt3 coding sequence or its complement.

The term "hybridization" as used herein includes "any process by which a strand of nucleic acid joins with a complementary strand through base pairing." [Coombs J (1994) *Dictionary of Biotechnology*, Stockton Press, New York N.Y.]. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

The phrase "hybridizes under stringent conditions" refers to the formation of a double-stranded duplex from two single-stranded nucleic acids. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid.

Nucleic acid probes to identify and clone DNA encoding polypeptides having the desired enzyme activity from strains of different genera or species can be prepared according to methods well known in the art. Such probes can be used for hybridization with the genomic or cDNA of the genus or species of interest, following standard Southern blotting procedures, in order to identify and isolate the corresponding gene therein. Both DNA and RNA probes can be used. The probes are typically labeled for detecting the corresponding gene (for example, with $^{32}P$, $^{3}H$, $^{35}S$, biotin, or avidin).

For purposes of this invention, it is preferred that probe hybridization of long probes of at least 100 nucleotides in length occurs under high stringency conditions. High stringency conditions when used in reference to nucleic acid hybridization comprise conditions equivalent to binding or hybridization at 68° C. in a solution consisting of 5×SSPE, 1% SDS, 5×Denhardt's reagent and 100 µg/ml denatured salmon sperm DNA followed by washing in a solution comprising 0.1×SSPE, and 0.1% SDS at 68° C. when a probe of about 100 to about 1000 nucleotides in length is employed, or the above-mentioned conditions with 50% formamide at 42° C. High stringency washes can include 0.1×SSC to 0.2×SSC, 1% SDS, 65° C., 15-20 min. An example of stringent wash conditions for a Southern blot of such nucleic acids is a 0.2×SSC wash at 65° C. for 15 minutes (see, Sambrook et al., Molecular Cloning—A Laboratory Manual ($2^{nd}$ ed.) Vol. 1-3, Cold Spring Harbor Laboratory, Cold Spring Harbor Press, NY, 1989, for a description of SSC buffer). Other exemplary high stringency hybridization conditions include, for example, 7% SDS, 0.25 M sodium phosphate buffer, pH 7.0-7.2, 0.25 M sodium chloride at 65° C.-68° C. or the above-mentioned conditions with 50% formamide at 42° C.

For short probes which are about 15 nucleotides to about 70 nucleotides in length, stringency conditions are defined as prehybridization, hybridization, and washing post-hybridization at about 5° C. about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the material with immobilized DNA is washed once in 6×SCC plus 0.1% SDS for 15 minutes and twice each for 15 minutes using 6×SSC at 5° C. about 10° C. below the calculated $T_m$.

A genomic DNA or cDNA library prepared from other organisms may be screened for DNA which hybridizes with the probes described above and which encodes a polypeptide having the desired enzyme activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable material. In order to identify a clone or DNA that is homologous with a selected sequence or a subsequence thereof, the material with immobilized DNA is used in a Southern blot. For purposes of the present invention, hybridization indicates that the nucleic acid sequence hybridizes to a labeled nucleic acid probe corresponding to the selected nucleic acid sequence, its complementary strand, or a subsequence thereof, under high stringency conditions. Molecules to which the nucleic acid probe hybridizes under these conditions are detected using X-ray film.

The RNA equivalents of the Sgt3 sequences are encompassed by the present invention.

Gene Silencing/Antisense constructs: Use of sequences and/or constructs in gene silencing or antisense uses are encompassed by the present invention. Without being bound by theory, it is submitted that the sequences encoding SGT3 activity, when used in gene silencing or antisense techniques, inhibit, decrease and/or prevent production of the SGT3 polypeptide and thereby reduce or eliminate SGT3 enzyme activity and reduce or eliminate accumulation of the steroidal glycoalkaloid end products shown in FIG. 1. This is based on the chemical analysis of product accumulation. In this case, the end products are reduced, and the immediate precursors are increased, thereby it is deduced that the function of the protein by its position in the biosynthetic pathway.

Down-regulation of expression of an Sgt3 gene may be achieved using anti-sense technology or "sense regulation" ("co-suppression"). In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al., 1987; Smith et al., (1988) Nature 334, 724-726; Zhang et al., (1992) The Plant Cell 4, 1575-1588, English et al., (1996) The Plant Cell 8, 179-188. Antisense technology is also reviewed in Bourque, (1995), Plant Science 105, 125-149, and Flavell, (1994) PNAS USA 91, 3490-3496. An alternative is to use a copy of all or part of the target gene inserted in sense, that is the same, orientation as the target gene, to achieve reduction in expression of the target gene by co-suppression. See, for example, van der Krol et al., (1990) The Plant Cell 2, 291-299; Napoli et al., (1990) The Plant Cell 2, 279-289; Zhang et al., (1992) The Plant Cell 4, 1575-1588, and U.S. Pat. No. 5,231,020. The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence. The sequence employed may be 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than 500 nucleotides may be used.

"Overexpression" in the context of the invention refers to the production of the SGT3 gene product in transgenic organisms that exceeds levels of production in normal or non-transformed organisms. Overexpression of the SGT3 enzyme of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same or different genes and also one or more introns in order to facilitate gene expression. 3' noncoding sequences encoding transcription termination signals may also be provided.

Crops in the Solanaceae family include potato (*Solanum tuberosum*); tomato (*Lysopersicon*, e.g., *L. lycopersicum* and *L. esculentum*); pepper (*Capsicum*); eggplant (*Solanum melongena*).

DETAILED DESCRIPTION OF THE INVENTION

The present invention is directed to the steroidal alkaloid glycosyl transferase enzyme β-solanine/β-chaconine rhamnosyltransferase (SGT3) which is involved in the biosynthesis of steroidal glycoalkaloids in Solanaceous plants. As discussed above, in cultivated potato the predominant glycoalkaloid species, α-chaconine and α-solanine, are triglycosylated derivatives of the aglycone solanidine. The final step in the synthesis of α-chaconine and α-solanine, is catalyzed by SGT3. The activity and kinetics of the enzyme SGT3 have not been demonstrated in vitro prior to our work and is demonstrated for the first time here using reverse genetics in transgenic plants. It is believed that decreasing the activity of the enzyme(s) responsible for the final glycosylation step should effectively lower the potential toxicity of potato cultivars.

In particular, the invention is directed to an isolated nucleic acid molecule encoding a SGT3 polypeptide selected from the group consisting of:

(a) a nucleic acid molecule with polypeptide coding sequence having at least 99% nucleotide sequence identity with SEQ ID NO:1 from nucleotide 7 to nucleotide 1521;

(b) a nucleic acid sequence which encodes a polypeptide having at least 99% identity with SEQ ID NO:2;

(c) a nucleic acid sequence which hybridizes under high stringency conditions with SEQ ID NO:1 from nucleotide 7 to nucleotide 1521;

(d) a nucleic acid molecule as shown in SEQ ID NO:1;

(e) an RNA equivalent of the sequences of (a), (b), (c), or (d); and (f) a complement of the molecule defined in (a), (b), (c), (d) or (e).

A specific embodiment of a Sgt3 nucleotide sequence is given in SEQ ID NO:1. This DNA sequence is 1671 bp in length. The open reading frame (coding portion), initiating at base 7 and terminating at base 1521 encodes a protein 505 amino acids in length (SEQ ID NO:2). The novel gene Sgt3 was obtained from the source organism *Solanum tuberosum*.

Further, nucleic acid sequences which hybridize under high stringency conditions, as defined above, with the coding region of the DNA sequence of SEQ ID NO:1 and which encode a polypeptide which encode a SGT3 polypeptide are included in the present invention.

The invention further encompasses a complementary strand of a nucleic acid sequence or RNA equivalent of the above sequences.

The present invention is also directed to recombinant host cells, comprising a nucleic acid sequence for recombinant production of the polypeptides or for gene silencing as described above. Preparation of transformed host cells and cloning methods are described by U.S. Pat. No. 5,374,540, which is incorporated herein by reference. Plants or seeds transformed with one or more of the sequences is encompassed by the invention. The transgenic plant may be constructed in accordance with methods known in the art. A specific example is set forth below.

A particular use of the nucleic acid sequences, portion thereof, complement or RNA equivalent is to inhibit SGT3 activity and reduce the levels of the steroidal glycoalkaloids α-chaconine and α-solanine in Solanaceous plants. SEQ ID NO:3 shows a SGT3 partial sequence that was used for construction of antisense constructs for the transgenic plant lines. This is described in detail in the Example below.

The present invention is also directed to isolated polypeptides having SGT3 activity, selected from the group consisting of:

(a) a polypeptide having at least 99% sequence identity with SEQ ID NO:2;

(b) a polypeptide encoded by a nucleic acid molecule with polypeptide coding sequence having at least 99% nucleotide sequence identity with SEQ ID NO:1 from nucleotide 7 to nucleotide 1521;

(c) a polypeptide encoded by a nucleic acid sequence which hybridizes under high stringency conditions with SEQ ID NOs:1 from nucleotide 7 to nucleotide 1521;

(d) a polypeptide having the amino acid sequence of SEQ ID NO:2.

Methods of Use.

The invention encompasses methods of use of the sequences and enzyme. A particular use of the nucleic acid sequences and portions thereof is to inhibit SGT3 activity and reduce the levels of the steroidal glycoalkaloids α-chaconine and α-solanine in Solanaceous plants. Another use of the nucleic acid sequences of the invention is to express SGT3 protein in bacteria or yeast by placing the full length SGT coding sequence under control of a suitable promoter and terminator. The promoter can be constitutive or inducible, depending upon the potential toxicity of the expressed protein. The protein can be expressed in its native configuration—unmodified, or can be fused to an antibody epitope or metal affinity tag to facilitate purification and in vitro biochemical analysis. Other uses of the sequences of the invention are to express or overexpress the SGT3 enzyme in a transgenic plant. The sequences of the invention can also be used as probes capable of detecting the Sgt3 gene or fragment thereof, and in methods to obtain purified SGT3.

EXAMPLE

The following example is intended only to further illustrate the invention and is not intended to limit the scope of the invention that is defined by the claims.

Materials and Methods

Plant Material

Meristems for DNA isolation were collected from control and transgenic potato (Solanum tuberosum L.) cv. Lenape grown in the glass house in Albany, Calif. For SGA and RNA analyses, Lenape tubers were harvested from replicated field plots in Aberdeen, Id. [Coetzer, et al., (2001) J. Agric. Food Chem., 49:652-657)] and Desirée tubers were harvested from glass house-grown plants in Invergowrie, Dundee, UK.

cDNA Sequence

Sgt3 sequences were identified in the TIGR EST database by protein homology with the deduced SGT1 sequence. At the onset of this investigation the Sgt3 EST sequences were assembled as two separate tentative consensus (TC) sequences in the TIGR database. Sgt3 cDNA sequences corresponding to the amino terminal TC were amplified by PCR using synthetic oligonucleotides [Forward: WRB 1439 TCAAAGTTACTATCATTGCCCCTC (SEQ ID NO:4), and Reverse: WRB 1440 GCAAACAAAGAGAACGGAGT-TAGG (SEQ ID NO:5)] from a wound induced tuber cDNA library prepared from Solanum tuberosum cv. Lemhi [Garbarino, et al., (1992) Plant Mol. Biol., 20:235-244). This N-terminal fragment was used for antisense construction. 5-prime and 3-prime ends of the cDNA were obtained using additional primers [WRB 1538 CCTACAGGTAATC-CAACTTC (SEQ ID NO:6) and WRB 1535 AAGGGTG-GCATATAGGTCC (SEQ ID NO:7), respectively) matched to λgt11 primer (WRB 1526 AACTGGTAATGGTAGCGACC (SEQ ID NO:8)]. Amplified fragments were cloned directly into pCR2.1 (TA cloning vector, Invitrogen).

Additional full length SGT3 coding sequences were amplified using primers at the 5-prime and 3-prime ends of the coding sequence [5-prime forward: WRB 1620 GGTAC-CATGGCGATGGAACAGAATGAAG (SEQ ID NO:9), and 3-prime reverse: WRB GGTACCTAAAAGGATTTCT-TGAAAGCACAAC (SEQ ID NO:10), or 3-prime reverse: WRB 1624 CTCGAGAAAGGATTTCTTGAAAGCA-CAAC (SEQ ID NO:11)]. Amplified fragments were cloned directly into the pYES2.1 expression vector (Invitrogen) with both the native stop codon (WRB 1621), and as a protein read-through fusion (WRB 1624) to the C-terminal tag in the vector. Identity of the Sgt3 sequence was verified using a functional approach of creating antisense transgenes and observing the effect on SGA metabolism in transgenic tubers.

Antisense Transgene Construction

Tuber-specific [van der Steege, et al., (1992) Plant Mol Biol, 20:19-30) transcription of the N-terminal portion of the Sgt3 CDS in antisense3 orientation is directed from a 1,206 bp potato GBSS6 promoter [van der Liej, et al., (1991) Mol Gen Genet, 228:240-248) and followed by a 404 bp potato ubi3 polyadenylation signal [Garbarino and Belknap, (1994) Plant Mol Biol, 24:119-127). An 805 bp fragment containing 785 bp of Sgt3 CDS (nucleotides 125 to 909 of the Sgt3 cDNA, SEQ ID NO:3) was excised with EcoRI from the pCR2.1 vector and ligated into the BamHI site of the pBin-PLUS/ARS_PGUT expression vector. pBinPLUS/ARS is a binary vector derived from pBinPLUS [van Engelen, et al., (1995) Transgenic Research, 4:288-290] that utilizes the ubiquitin promoter and terminator sequences (Ubi3) to drive the NptII selectable marker gene.

Plant Transformation with Antisense Transgene Construct

The antisense transgene construct was mobilized into potato varieties Lenape [Akeley, et al., (1968) American Potato Journal, 45:142-151) and Desirée via Agrobacterium-mediated transformation [Snyder and Belknap, (1993) Plant Cell Reports, 12:324-327).

Steroidal Glycoalkaloid Determinations

Levels of steroidal glycoalkaloids (SGAs) were quantified in slices of tubers or whole minitubers of field-grown Lenape or glass house-grown Desiree, respectively. Field-grown tubers were cut in half longitudinally through the widest dimension ~2.5 mm off center with a chef knife and the central longitudinal section of 5 mm was cut with a mandolin. Sections were frozen in liquid nitrogen, freeze dried, milled and the dry powder extracted and analyzed for SGAs by HPLC as described by Hellenas [Hellenaes, (1986) J Sci Food Agri, 37:776-782]. MS analysis was preformed using a Thermo Finnigan LCQ-DECA with Ion trap, MS and data-dependent MS/MS on base peak ion, 45NCE, wideband activation. Reserpine was used as an internal standard (2 μM), calibration with authentic α-solanine and α-chaconine standards in 2 μM reserpine to calculate response factors for these two analytes.

RNA Blots

To examine the wounding response, total RNA was prepared from tuber peels obtained using a hand-held vegetable peeler. Peels were frozen in liquid nitrogen, powdered and extracted for RNA as previously described [Verwoerd, et al., (1989) Nucleic Acids Res., 17:2362]. To examine antisense transgene mRNA abundance, RNA was fractionated by agarose gel electrophoresis, transferred to a nylon membrane (Roche) [Rickey and Belknap, (1991) Plant Mol. Biol., 16:1009-1018]. RNA blots were hybridized with a random primed (GE healthcare) double stranded probe of the Sgt3 cDNA isolated from clones borne in pCR2.1 by digestion with EcoRI.

DNA Blots

DNA was isolated from young shoot tips frozen in liquid nitrogen and extracted as previously described [Draper and Scott, (1988) Plant Genetic Transformation and Gene Expression: A Laboratory Manual:199-236]. DNA was digested with the restriction endonuclease HindIII and separated by agarose electrophoresis, blotted to nylon, and hybridized with a double stranded Sgt3 probe containing the complete coding sequence.

Results

Sgt3 Sequence Identity and Protein Homology

Identification of the SGT3 encoding sequence was accomplished by screening the TIGR expressed sequence tag (EST) database of expressed potato genes. The EST database was searched for sequences whose predicted protein translation contained homology to the known SGT1 [Moehs, et al., (1997) Plant J., 11:227-236] sequence for UDP-glycosyl transferase and steroid recognition domains. The candidate sequences were then further screened for their expression profiles as determined by abundance of ESTs and tissue source as compared to Sgt1. Using primers to the EST sequence, 5 clones (4 identical) were obtained representing the amino terminal region from +119 to +903 of the longest open reading frame (SEQ ID NO:3). The 4 longer Sgt3 clones were 785 bp, and the insert from one was used to construct an antisense vector for transformation into potato. The 5-prime and 3-prime cDNA ends were obtained in separate rounds of PCR using sequences internal to the putative Sgt coding sequence. Three independent clones of different lengths were obtained for the 5-prime sequence. Only the longest of these contained an additional methionine start codon representative of the longest possible open reading frame. This clone was 262 bp and possessed 6 bp of 5-prime untranslated sequence. Three independent clones were obtained for the 3-prime sequence. The longest clone was 935 bp with a 3-prime untranslated region (3'UTR) of 141 bp and a poly(A) tail of 6 bases. Of the remaining two clones, one had the same length 3'UTR without a poly(A) tail and the third clone (898 bp) had a shorter 3'UTR (109 bp) and a poly(A) tail of 11 bases. This establishes functional polymorphism in polyadenylation sites. Each of the three sequences obtained had a unique single nucleotide polymorphism in the CDS, and one had an additional polymorphism in the 3'UTR.

Using primers to the ends of the CDS, 12 additional clones were obtained. These were used to generate a consensus for the predicted amino acid sequence of SGT3. Most clones contained at least one unique nucleotide polymorphism, and only one clone had a sequence identical to the consensus.

Using the sequences of the amino terminal, CDS, and flanking 5-prime and 3-prime fragments a consensus cDNA of 1671 bp has been assembled and is designated SOLtu:Sgt3 (SEQ ID NO:1; GenBank Accession Number DQ266437) and contains an open reading frame encoding a 505 residue polypeptide.

The consensus Sgt3 cDNA isolated from *S. tuberosum* cv. Lemhi shows a 100% identity to the latest TC sequence assemblage of Sgt3 ESTs in the TIGR database. Comparing the coding sequence of Sgt3 to the sequence of Sgt1, the previously identified potato sterol alkaloid galactosyltransferase, shows 64% nucleic acid identity (FIG. 2). This indicates that an antisense approach to silence both genes simultaneously would not work. Predicted protein alignment of SGT3 and SGT1 shows the putative substrate binding recognition portion (amino acids #s 108-145) of the amino-terminus, homologous in a number of glycosyltransferases, and the rhamnose binding region (amino acid #s 351-401) including the potential active site histidine residues [Nawloka, et al., (2003) Acta Biochim. Pol., 50:567-572) in the carboxy-terminus.

Occurrence of the Sgt3 Locus in *S. tuberosum*

Figure 4:
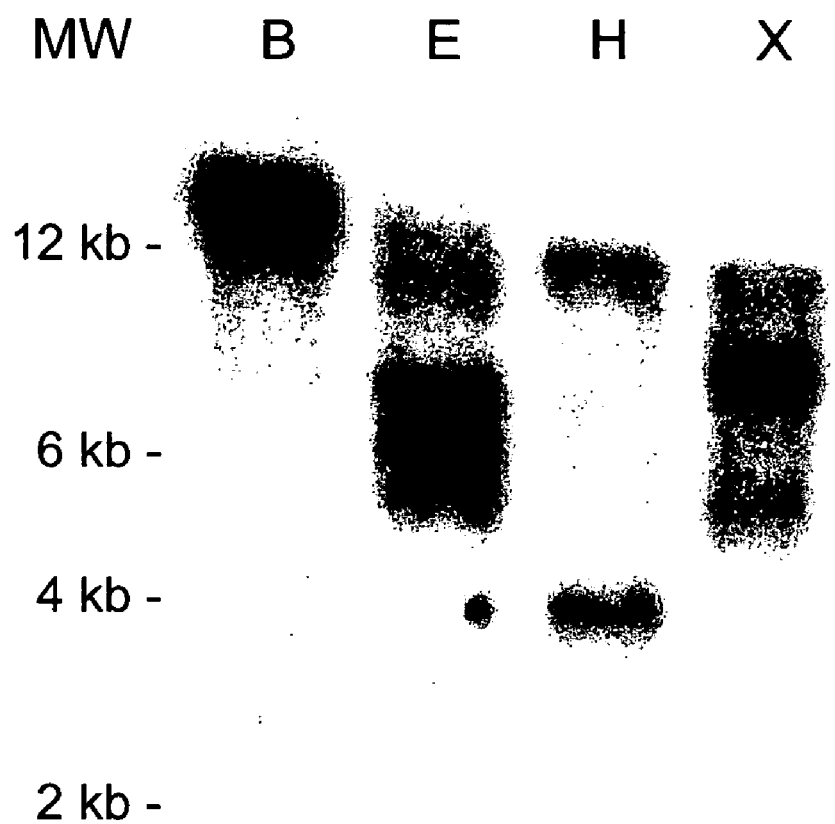
FIG. 4 shows the occurrence of Sgt3 in the potato genome. DNA blot analysis using restriction endonucleases as indicated in the figure for S. tuberosum cv. Lenape. Sgt3 is a low copy gene in the potato genome with 2 to 4 copies likely representative of a single allele on each of the chromosome homologs and homoeologues.

The approximate copy number and variation of genes in *S. tuberosum* was evaluated in a genomic blot. FIG. 4 shows the relative banding patterns using 4 different restriction endonucleases to examine copy number. The relatively small number of bands, and expected presence of up to 4 alleles suggests that Sgt3 is a single copy gene on each of the 4 potato homoeologs.

Steroidal Glycoalkaloid Accumulation

Figure 5A:
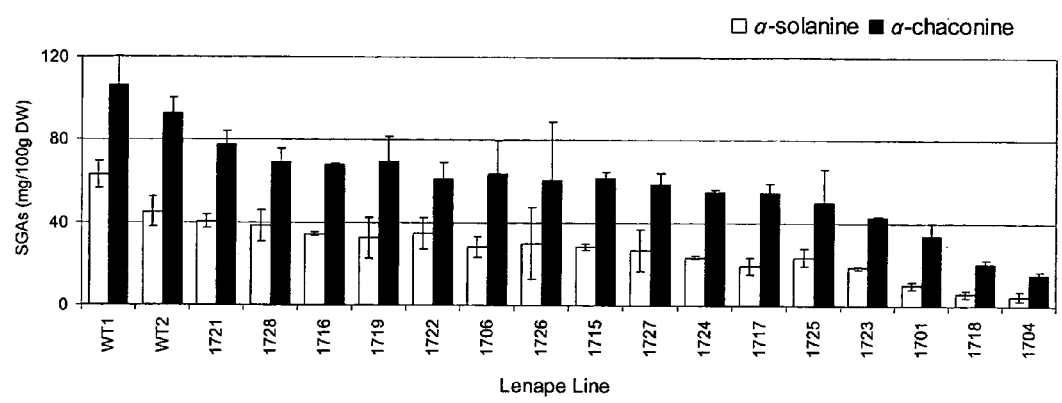
FIG. 5 shows SGA content of tubers from transgenic potatoes expressing the Sgt3 antisense transgene. Total SGA levels showing the range of alkaloids accumulated in selected transgenic, wild type (WT) and empty vector (MT) control lines of Lenape (FIG. 5A) and Desiree (FIG. 5B). Values represent data from a single glass house-grown minitubers (Desiree) or slices from 2 replicates of field-grown tubers (Lenape).
Figure 5B:
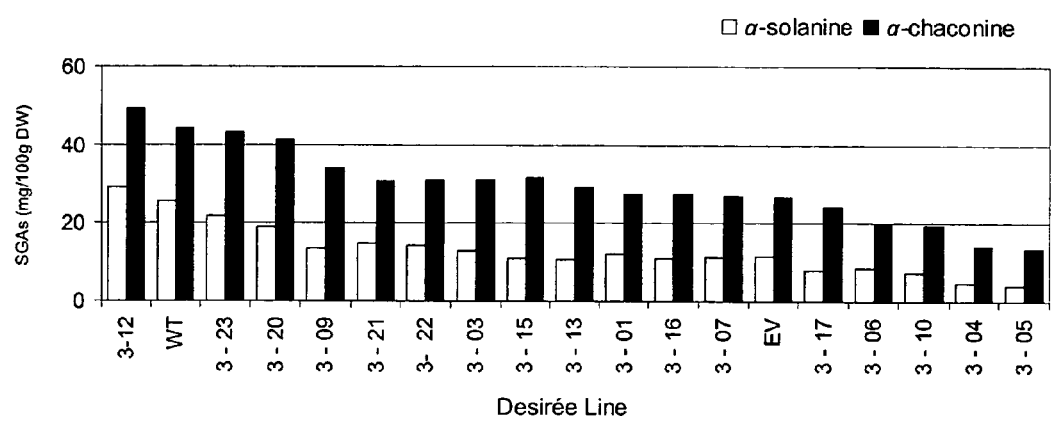

The levels of α-solanine and α-chaconine were measured in uniform slices of field grown Lenape tubers (FIG. 5a) or whole glass house grown Desiree minitubers (FIG. 5b). The data in the figure presents the lines sorted by descending levels of total α-SGAs (α-solanine+α-chaconine). The range in α-SGAs for Sgt3 antisense lines varied from 11% above to 87% below wild type and is similar for both the replicated field plots and T1 greenhouse lines. This variation exceeds that seen previously where variation of +/−30-40% is within the range attributable to somaclonal variation [Esposito, et al., (2002) J. Agric. Food Chem. 50:1553-1561]. Levels of α-solanine and α-chaconine were reduced as much as 91 and 85%, respectively in Lenape and 84 and 70%, respectively in Desirée. The reductions for both α-solanine and α-chaconine in Lenape lines 1701, 1704 and 1718 were significantly reduced compared to controls (p>0.001).

Analysis of Transgene Integration

Figure 6:
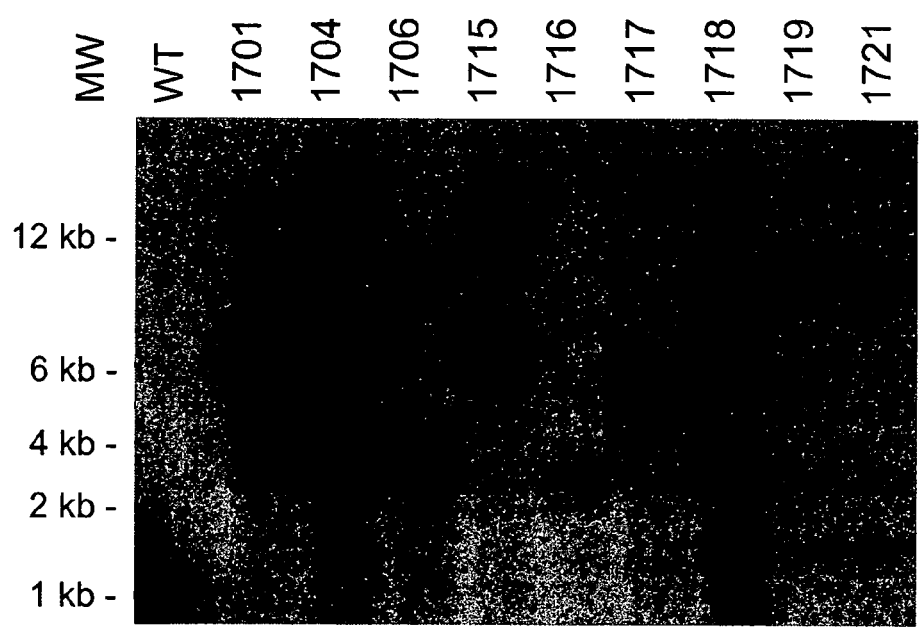
FIG. 6 shows integration patterns of antisense Sgt3 transgene in Lenape lines. Genomic blot analysis of Sgt3 in control and transgenic lines of Lenape. Genomic DNA was digested with HinDEi and probed with the complete Sgt3 coding sequence.

An examination of the integration patterns in select transgenic lines was carried out by genomic DNA Southern blot analysis using either Sgt3 (FIG. 6a) or NptII (FIG. 6b) as probes. The ethidium bromide stained gel shows loading consistency and DNA integrity (FIG. 6c). The results reveal a simple pattern in lines 1716, 1719 and 1721 suggesting one or two insertions. Lines 1706, 1715 and 1717 are intermediate with heavier banding and likely 2 to 3 insertions. In lines 1701, 1704 and 1718, complex patterns are observed particularly in the NptII-probed blot, indicating multiple insertions.

Expression of Antisense Sgt3

To examine the affect of transgene integration on antisense transgene expression, the steady state level of Sgt3 RNA was examined. RNA was isolated from transgenic lines and probed with the Sgt3 sequence. Transgenic lines with reduced steady state levels of Sgt3 transcripts were observed, including some completely lacking endogenous transcripts (lines 1701 and 1704), and some with degraded transcripts (lines 1701, 1717 and 1718), suggestive of functional antisense transgenes where both sense and antisense message are quickly degraded resulting in effective elimination of the target protein [Robert, et al., (1989) Plant Mol Biol, 13:399-409).

Analysis of Component Steroidal Glycoalkaloids

Figure 7A:
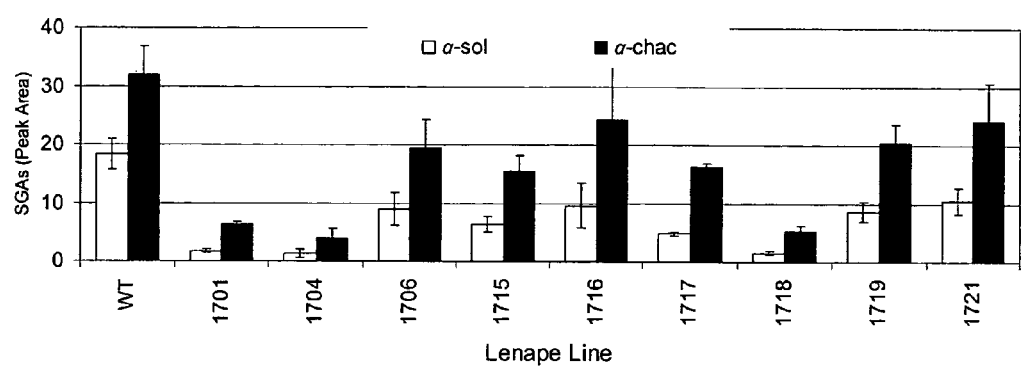
FIGS. 7A, B and C show analysis of selected Sgt3 antisense transgenic lines. LC-MS Analysis of component alkaloids: α-solanine and α-chaconine (FIG. 7A); γ-solanine/chaconine, β-solanine and P-chaconine (FIG. 7B); and putative malonylated derivatives of α- and β-chaconine, (FIG. 7C) in transgenic Lenape lines. Peak area values represent the average and standard deviation of 3 samples from individual field-grown tubers.
Figure 7B:
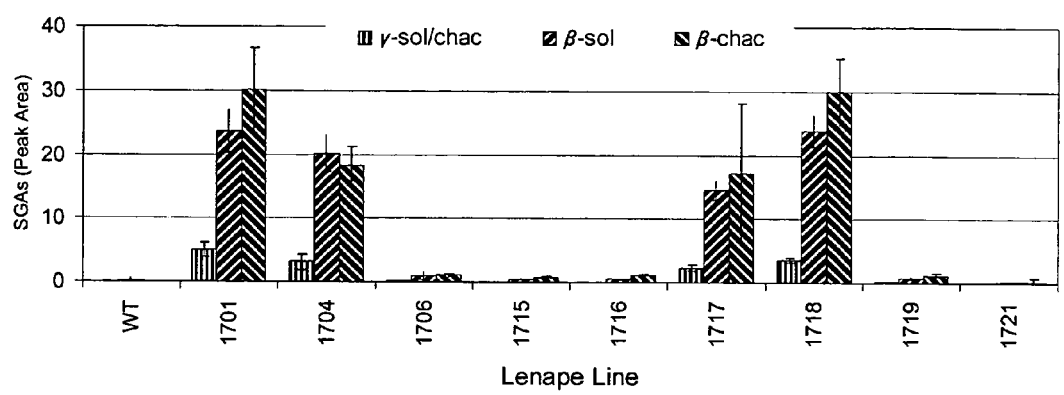
Figure 7C:
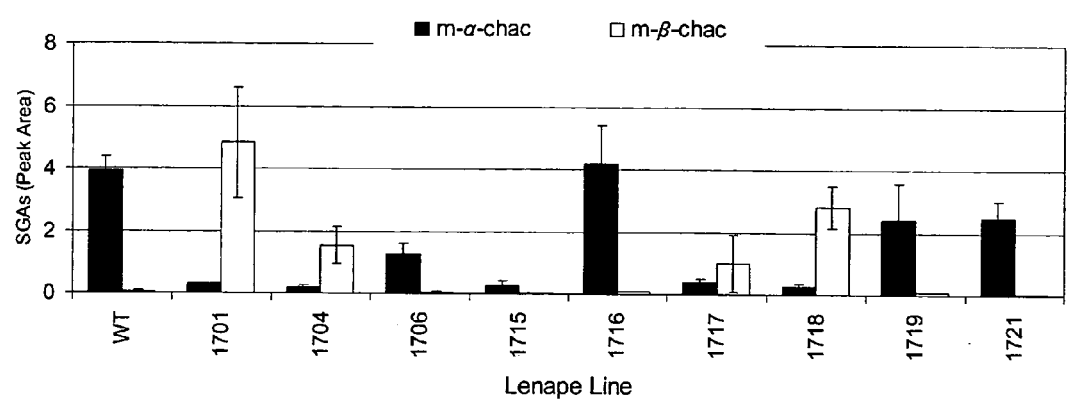

In a more detailed examination of SGAs by LC-MS, the relative levels of intermediates and products of the SGA biosynthetic pathway were examined in selected Sgt3 transgenic lines (FIG. 7). Analysis revealed a dramatic change in the levels of specific SGA precursors and products in some of the Sgt3 antisense lines. A number of lines in each population produced tubers in which levels of both α-chaconine and α-solanine were significantly decreased (Lenape lines 1701, 1704, 1717, and 1718).

LC-MS analysis indicates that inhibition of α-solanine and α-chaconine was accompanied by the accumulation of both β-solanine and β-chaconine as well as minor accumulation of γ-solanine and γ-chaconine (not separable). A product tentatively identified as the malonylated derivate of α-chaconine accumulates in WT and transgenic lines with normal levels of α-solanine and α-chaconine and is significantly absent in the suppressed lines. In these suppressed lines (1701, 1704, 1717, and 1718), the appearance of an additional peak consistent with the production of malonylated β-chaconine is observed. Reductions of both α-chaconine and α-solanine accumulation have now been observed in additional Desiree and Lenape lines (data not shown). Down-regulation of SGT3 in lines expressing effective Sgt3 antisense transgenes had significant reductions in solanine >80% and chaconine >70%.

The Sgt3 gene sequences were isolated by PCR from a wound-induced tuber cDNA library from cv Lemhi. The initial Sgt3 primers were directed to the amino terminal TC sequence identified in the TIGR database as encoding a protein with high homology to SGT1, the previously identified steroidal alkaloid galactosyl transferase. Using internal primers to the amplified sequence, the 5-prime and 3-prime flanking sequences were isolated by PCR from the same cDNA library. A search of the TIGR potato EST database with the 1671 bp Sgt3 consensus mRNA sequence returned two high identity (99%) matches for the Sgt3 cDNA. The first is the TC sequence originally identified with homology to SGT1 used to design synthetic oligonucleotides used for the isolation of the Sgt3 amino terminal encoding fragment. The four longest ESTs in this TC sequence contain 23, 53(2) and 88 nucleotides of 5'UTR relative to the longest cDNA from cv. Lemhi. The second TC sequence aligns to the 3-prime end of the assembled Sgt3 cDNA. Of the three 3-prime ESTs in the database, all three appear to utilize the distal polyadenylation site. The third most closely related TC sequence (61%) is the original potato Sgt1 TC sequence. A blast search of the GenBank non-redundant nucleotide sequence database returns no significant sequence identities when searched with the Sgt3 nucleotide sequence.

Antisense transgenes have been successfully employed to down-regulate target genes in potato [Taylor, et al., (2000) Plant J., 24:305-316; Zeh, et al., (2001) Plant Physiol., 127: 792-802). Effective down-regulation is expected in 5-10% of the antisense RNA-expressing lines [Coetzer, et al., (2001) J. Agric. Food Chem., 49:652-657). A total of 45 lines have been developed using the Sgt3 antisense construct described above. Analysis of SGA levels produced a continuum of values. In Desirée, The sum of α-solanine plus α-chaconine ranged from 17 to 77% of control in Lenape, and from 25 to 112% in Desirée. It is currently not possible to accurately calculate quantitative values for all the SGA intermediates (β- and γ-solanine and chaconine and malonylated derivatives) and calculate a sum for the total SGA level, due to an absence of standards to construct the calibration curves that take into account the different degrees to which the various intermediates ionize.

Previous examination of Sgt1 antisense lines for transgene integration revealed complex genomic integration patterns in lines with altered chemotypes [McCue et. al., (2005) Plant Sci. 168:267-273]. A similar pattern of transgene integration was observed in the Lenape antisense lines. Lines showing reduced levels of α-SGAs had more complex integration patterns.

A similar correlation is found in the steady state levels of Sgt3 RNA. Plant lines with complex integration patterns tend to have reduced or absent message for Sgt3 indicative of effective antisense suppression.

The molecular evidence for the action of an effective antisense Sgt3 transgene coupled with the chemical analysis of transgenic plants expressing the suppression construct allows us to assign the function of SGT3 as the β-steroidal glycoalkaloid rhamnosyltransferase responsible for the conversion of β-solanine and β-chaconine to α-solanine and α-chaconine, respectively, in potato glycoalkaloid biosynthesis.

It is understood that the foregoing detailed description is given merely by way of illustration and that modification and variations may be made within, without departing from the spirit and scope of the invention. All publications, patents, published applications, and sequence listings cited herein are hereby incorporated by reference in their entirety.

What is claimed is:

1. An isolated nucleic acid molecule encoding a β-solanine/β-chaconine rhamnosyltransferase (SGT3) polypeptide having SGT3 enzymatic activity, selected from the group consisting of:

(a) a nucleic acid molecule with polypeptide coding sequence having at least 99% nucleotide sequence identity with SEQ ID NO:1 from nucleotide 7 to nucleotide 1521;

(b) a nucleic acid sequence which encodes a polypeptide having at least 99% identity with SEQ ID NO:2;

(c) a nucleic acid sequence which hybridizes under high stringency conditions with: SEQ ID NO:1 from nucleotide 7 to nucleotide 1521 wherein said high stringency conditions comprise hybridization at 68° C. in a solution consisting of 5×SSPE, 1% SDS 5×Denhardt's reagent and 100 µg/ml denatured salmon sperm DNA followed by washing in a solution comprising 0.1×SSPE, and 0.1% SDS at 68° C.;

(d) a nucleic acid molecule as shown in SEQ ID NO:1;

(e) an RNA equivalent of the sequences of (a), (b), (c), or (d); and (f) a full length complement of the molecule defined in (a), (b), (c), (d) or (e).

2. A nucleic acid construct comprising the nucleic acid molecule of claim 1 operably linked to one or more control sequences that direct the regulation of SGT3 polypeptide in an expression host.

3. A cell transformed with the isolated nucleic acid molecule of claim 1.

4. A plant transformed with the isolated nucleic acid molecule of claim 1.

5. A seed of the plant according to claim 4, wherein said seed is transgenic and contains said isolated nucleic acid molecule.

6. The plant of claim 4 wherein the plant is a Solanaceous plant.

7. The plant of claim 6 wherein the Solanaceous plant is potato.

8. Sexually or asexually derived progeny of the plant of claim 4, wherein said progeny is transgenic and contains said isolated nucleic acid molecule.

9. A method of producing a polypeptide having SGT3 activity, which comprises cultivating a transformed host cell have the nucleic acid molecule of claim 1 which encodes a SGT3 polypeptide, under conditions suitable for production of the polypeptide; and recovering the polypeptide.

10. The method of claim 9, wherein said polypeptide is produced at a level exceeding that in a non-transformed cell.

* * * * *

SEQUENCE LISTING

<160> NUMBER OF SEQ ID NOS: 19

<210> SEQ ID NO 1
<211> LENGTH: 1671
<212> TYPE: DNA
<213> ORGANISM: Solanum Tuberosum Sgt3
<220> FEATURE:
<221> NAME/KEY: CDS
<222> LOCATION: (7)..(1521)

<400> SEQUENCE: 1

```
ttgtta atg gcg atg gaa cag aat gaa gaa act gca atg ccg cat gtt      48
       Met Ala Met Glu Gln Asn Glu Glu Thr Ala Met Pro His Val
       1               5                  10
```

-continued

| | |
|---|---|
| gtg ttc ata cca tac gcc atg acg agt cat ata act cca ttg gta cat<br>Val Phe Ile Pro Tyr Ala Met Thr Ser His Ile Thr Pro Leu Val His<br>15                      20                        25                      30 | 96 |
| att gct aga ctc ttc gcc ctc cat ggc ctc aaa gtt act atc att gcc<br>Ile Ala Arg Leu Phe Ala Leu His Gly Leu Lys Val Thr Ile Ile Ala<br>                35                        40                        45 | 144 |
| cct cag cat aat gct ctt ctt ttt cag tcc tct gtc gat aga gac cgt<br>Pro Gln His Asn Ala Leu Leu Phe Gln Ser Ser Val Asp Arg Asp Arg<br>            50                        55                        60 | 192 |
| ctc ttt tcg ggc agc aat att act gtc cgg aca att caa ttt ccg tct<br>Leu Phe Ser Gly Ser Asn Ile Thr Val Arg Thr Ile Gln Phe Pro Ser<br>        65                        70                        75 | 240 |
| gag gaa gtt gga tta cct gta gga att gaa aac ttc atc gca agc cct<br>Glu Glu Val Gly Leu Pro Val Gly Ile Glu Asn Phe Ile Ala Ser Pro<br>80                      85                        90 | 288 |
| tct atg gaa ata gtt ggc aaa gtt cac tat ggg ttt att ctg ctc caa<br>Ser Met Glu Ile Val Gly Lys Val His Tyr Gly Phe Ile Leu Leu Gln<br>95                      100                   105             110 | 336 |
| aag att atg gag caa cta att cgg gag atc aat cca aac tgc att gtt<br>Lys Ile Met Glu Gln Leu Ile Arg Glu Ile Asn Pro Asn Cys Ile Val<br>                115                   120             125 | 384 |
| tcc gat atg ttc ttc cct tgg act gtt gat tta gct gag gag atg caa<br>Ser Asp Met Phe Phe Pro Trp Thr Val Asp Leu Ala Glu Glu Met Gln<br>            130                   135             140 | 432 |
| att ccg aga ttt tct ttt caa cca gcc act tcc ata cat caa tgt gct<br>Ile Pro Arg Phe Ser Phe Gln Pro Ala Thr Ser Ile His Gln Cys Ala<br>                145                   150             155 | 480 |
| tgg gtt ttc atc agg gaa ttt aaa cct tac aag aat gtg gcg tcg gat<br>Trp Val Phe Ile Arg Glu Phe Lys Pro Tyr Lys Asn Val Ala Ser Asp<br>160                     165                   170 | 528 |
| gct gaa aag ttt ttg att cct ggt ttg cct ctc gac atc aaa atg aaa<br>Ala Glu Lys Phe Leu Ile Pro Gly Leu Pro Leu Asp Ile Lys Met Lys<br>175                     180                   185             190 | 576 |
| gtc tca gag att gaa gat ttt ctt aaa gag gaa act gag tac aca aag<br>Val Ser Glu Ile Glu Asp Phe Leu Lys Glu Glu Thr Glu Tyr Thr Lys<br>                195                   200             205 | 624 |
| aca gta gat gac gtt tta caa gct gag gtt cgt agc cat ggt att att<br>Thr Val Asp Asp Val Leu Gln Ala Glu Val Arg Ser His Gly Ile Ile<br>            210                   215             220 | 672 |
| cat aac act tgc tct gag ctg gaa cct ggc gtt gcc caa ctc tac gaa<br>His Asn Thr Cys Ser Glu Leu Glu Pro Gly Val Ala Gln Leu Tyr Glu<br>                225                   230             235 | 720 |
| aaa gct aga gga gta aaa ggg tgg cat ata ggt cca ctt gct ctg ttt<br>Lys Ala Arg Gly Val Lys Gly Trp His Ile Gly Pro Leu Ala Leu Phe<br>240                     245                   250 | 768 |
| atc aac aaa tat gaa gcg gaa att agt tct aaa caa att tcc aat tcg<br>Ile Asn Lys Tyr Glu Ala Glu Ile Ser Ser Lys Gln Ile Ser Asn Ser<br>255                     260                   265             270 | 816 |
| aat att aat tca tgt tct gac cct tgg aaa ggg tac ggt gat tgt ttc<br>Asn Ile Asn Ser Cys Ser Asp Pro Trp Lys Gly Tyr Gly Asp Cys Phe<br>                275                   280             285 | 864 |
| aat tgg ctt gaa aat caa caa cct aac tcc gtt ctc ttt gtt tgc ttt<br>Asn Trp Leu Glu Asn Gln Gln Pro Asn Ser Val Leu Phe Val Cys Phe<br>            290                   295             300 | 912 |
| gga agc atg ata aga ttt tcc gat gat cag ctt aag gaa atg gct gtt<br>Gly Ser Met Ile Arg Phe Ser Asp Asp Gln Leu Lys Glu Met Ala Val<br>                305                   310             315 | 960 |
| gga ttg aag gct gcc aac tgt cca act att tgg gtt ttt agg gag cag<br>Gly Leu Lys Ala Ala Asn Cys Pro Thr Ile Trp Val Phe Arg Glu Gln<br>320                     325                   330 | 1008 |

```
gac aaa aat gaa gta gac gag aaa gat gag cat tct gac tgg agc cgt     1056
Asp Lys Asn Glu Val Asp Glu Lys Asp Glu His Ser Asp Trp Ser Arg
335             340             345             350 aat ggt ttc aaa gaa atg att ggg gaa aag atg ttt atc atc caa ggc     1104
Asn Gly Phe Lys Glu Met Ile Gly Glu Lys Met Phe Ile Ile Gln Gly
            355             360             365 tgg gca cca caa caa tta atc ctg aaa cat caa gca att ggt gga ttc     1152
Trp Ala Pro Gln Gln Leu Ile Leu Lys His Gln Ala Ile Gly Gly Phe
        370             375             380 tta act cat tgt ggt tgg aac tct ata ctt gag tct cta gcc gta ggt     1200
Leu Thr His Cys Gly Trp Asn Ser Ile Leu Glu Ser Leu Ala Val Gly
    385             390             395 gtt cca ttg atc aca tgg cca ctt ttc tca gac aac ttc tat acc gac     1248
Val Pro Leu Ile Thr Trp Pro Leu Phe Ser Asp Asn Phe Tyr Thr Asp
400             405             410 aag ctt ttg gag aca ctt ggc ctt gct att gga att gga gca gat gtg     1296
Lys Leu Leu Glu Thr Leu Gly Leu Ala Ile Gly Ile Gly Ala Asp Val
415             420             425             430 tgg aat ccg ggg ttt ata tta tcg tgt cca ccc ctt tca gga gag aag     1344
Trp Asn Pro Gly Phe Ile Leu Ser Cys Pro Pro Leu Ser Gly Glu Lys
            435             440             445 ata gag ttg gcc gtc aag cgt tta atg aat aat tca gag gaa agt aga     1392
Ile Glu Leu Ala Val Lys Arg Leu Met Asn Asn Ser Glu Glu Ser Arg
        450             455             460 aaa att aga gaa aat gca aag ttg atg gca aag aag ctc aaa agt gcc     1440
Lys Ile Arg Glu Asn Ala Lys Leu Met Ala Lys Lys Leu Lys Ser Ala
    465             470             475 act gaa gaa ggt ggt tcc tct cat tca cag ctt atc ggg tta att gag     1488
Thr Glu Glu Gly Gly Ser Ser His Ser Gln Leu Ile Gly Leu Ile Glu
480             485             490 gag atc aag cgt tgt gct ttc aag aaa tcc tct tgaaatttta tgttttactt  1541
Glu Ile Lys Arg Cys Ala Phe Lys Lys Ser Ser
495             500             505 atcactttga aataaatttg gcaaatggag tttggtcaac attaacaatg tatctggtct   1601 taattttttgt ttaaatgcat gctttgcagt gtcatttgtc attagtgaaa cattaaatct  1661
taataaaaaa                                                          1671

<210> SEQ ID NO 2
<211> LENGTH: 505
<212> TYPE: PRT
<213> ORGANISM: Solanum Tuberosum Sgt3

<400> SEQUENCE: 2

Met Ala Met Glu Gln Asn Glu Glu Thr Ala Met Pro His Val Val Phe
1               5                   10                  15

Ile Pro Tyr Ala Met Thr Ser His Ile Thr Pro Leu Val His Ile Ala
            20                  25                  30

Arg Leu Phe Ala Leu His Gly Leu Lys Val Thr Ile Ala Pro Gln
        35                  40                  45

His Asn Ala Leu Leu Phe Gln Ser Ser Val Asp Arg Asp Arg Leu Phe
    50                  55                  60

Ser Gly Ser Asn Ile Thr Val Arg Thr Ile Gln Phe Pro Ser Glu Glu
65                  70                  75                  80

Val Gly Leu Pro Val Gly Ile Glu Asn Phe Ile Ala Ser Pro Ser Met
            85                  90                  95

Glu Ile Val Gly Lys Val His Tyr Gly Phe Ile Leu Leu Gln Lys Ile
            100                 105                 110
```

Met Glu Gln Leu Ile Arg Glu Ile Asn Pro Asn Cys Ile Val Ser Asp
                115                 120                 125

Met Phe Phe Pro Trp Thr Val Asp Leu Ala Glu Glu Met Gln Ile Pro
    130                 135                 140

Arg Phe Ser Phe Gln Pro Ala Thr Ser Ile His Gln Cys Ala Trp Val
145                 150                 155                 160

Phe Ile Arg Glu Phe Lys Pro Tyr Lys Asn Val Ala Ser Asp Ala Glu
                165                 170                 175

Lys Phe Leu Ile Pro Gly Leu Pro Leu Asp Ile Lys Met Lys Val Ser
            180                 185                 190

Glu Ile Glu Asp Phe Leu Lys Glu Thr Glu Tyr Thr Lys Thr Val
            195                 200                 205

Asp Asp Val Leu Gln Ala Glu Val Arg Ser His Gly Ile Ile His Asn
    210                 215                 220

Thr Cys Ser Glu Leu Glu Pro Gly Val Ala Gln Leu Tyr Glu Lys Ala
225                 230                 235                 240

Arg Gly Val Lys Gly Trp His Ile Gly Pro Leu Ala Leu Phe Ile Asn
                245                 250                 255

Lys Tyr Glu Ala Glu Ile Ser Ser Lys Gln Ile Ser Asn Ser Asn Ile
                260                 265                 270

Asn Ser Cys Ser Asp Pro Trp Lys Gly Tyr Gly Asp Cys Phe Asn Trp
            275                 280                 285

Leu Glu Asn Gln Gln Pro Asn Ser Val Leu Phe Val Cys Phe Gly Ser
        290                 295                 300

Met Ile Arg Phe Ser Asp Asp Gln Leu Lys Glu Met Ala Val Gly Leu
305                 310                 315                 320

Lys Ala Ala Asn Cys Pro Thr Ile Trp Val Phe Arg Glu Gln Asp Lys
                325                 330                 335

Asn Glu Val Asp Glu Lys Asp Glu His Ser Asp Trp Ser Arg Asn Gly
            340                 345                 350

Phe Lys Glu Met Ile Gly Glu Lys Met Phe Ile Ile Gln Gly Trp Ala
        355                 360                 365

Pro Gln Gln Leu Ile Leu Lys His Gln Ala Ile Gly Gly Phe Leu Thr
    370                 375                 380

His Cys Gly Trp Asn Ser Ile Leu Glu Ser Leu Ala Val Gly Val Pro
385                 390                 395                 400

Leu Ile Thr Trp Pro Leu Phe Ser Asp Asn Phe Tyr Thr Asp Lys Leu
                405                 410                 415

Leu Glu Thr Leu Gly Leu Ala Ile Gly Ile Gly Ala Asp Val Trp Asn
            420                 425                 430

Pro Gly Phe Ile Leu Ser Cys Pro Pro Leu Ser Gly Glu Lys Ile Glu
        435                 440                 445

Leu Ala Val Lys Arg Leu Met Asn Asn Ser Glu Ser Arg Lys Ile
    450                 455                 460

Arg Glu Asn Ala Lys Leu Met Ala Lys Leu Lys Ser Ala Thr Glu
465                 470                 475                 480

Glu Gly Gly Ser Ser His Ser Gln Leu Ile Gly Leu Ile Glu Glu Ile
                485                 490                 495

Lys Arg Cys Ala Phe Lys Lys Ser Ser
                500                 505

<210> SEQ ID NO 3
<211> LENGTH: 785

<212> TYPE: DNA
<213> ORGANISM: Solanum tuberosum

<400> SEQUENCE: 3

```
tcaaagttac tatcattgcc cctcagcata atgctcttct ttttcagtcc tctgtcgata    60
gagaccgtct cttttcgggc agcaatatta ctgtccggac aattcaattt ccgtctgagg   120
aagttggatt acctgtagga attgaaaact tcatcgcaag cccttctatg gaaatagttg   180
gcaaagttca ctatgggttt attctgctcc aaaagattat ggagcaacta attcgggaga   240
tcaatccaaa ctgcattgtt tccgatatgt tcttcccttg gactgttgat ttagctgagg   300
agatgcaaat tccgagattt tcttttcaac cagccacttc catacatcaa tgtgcttggg   360
ttttcatcag ggaatttaaa ccttacaaga atgtggcgtc ggatgctgaa aagttttga   420
ttcctggttt gcctctcgac atcaaaatga aagtctcaga gattgaagat tttcttaaag   480
aggaaactga gtacacaaag acagtagatg acgttttaca agctgaggtt cgtagccatg   540
gtattattca taacacttgc tctgagctgg aacctggcgt tgcccaactc tacgaaaaag   600
ctagaggagt aaaagggtgg catataggtc cacttgctct gtttatcaac aaatatgaag   660
cggaaattag ttctaaacaa atttccaatt cgaatattaa ttcatgttct gaccctggga   720
aagggtacgg tgattgtttc aattggcttg aaaatcaaca acctaactcc gttctctttg   780
tttgc                                                               785
```

<210> SEQ ID NO 4
<211> LENGTH: 24
<212> TYPE: DNA
<213> ORGANISM: Artificial
<220> FEATURE:
<223> OTHER INFORMATION: Primer WRB 1439-Forward

<400> SEQUENCE: 4

```
tcaaagttac tatcattgcc cctc                                           24
```

<210> SEQ ID NO 5
<211> LENGTH: 24
<212> TYPE: DNA
<213> ORGANISM: Artificial
<220> FEATURE:
<223> OTHER INFORMATION: Primer WRB 1440-Reverse

<400> SEQUENCE: 5

```
gcaaacaaag agaacggagt tagg                                           24
```

<210> SEQ ID NO 6
<211> LENGTH: 20
<212> TYPE: DNA
<213> ORGANISM: Artificial
<220> FEATURE:
<223> OTHER INFORMATION: Primer WRB 1538 SGT3 R326 - Sgt3 5-prime
      Reverse

<400> SEQUENCE: 6

```
cctacaggta atccaacttc                                                20
```

<210> SEQ ID NO 7
<211> LENGTH: 19
<212> TYPE: DNA
<213> ORGANISM: Artificial
<220> FEATURE:
<223> OTHER INFORMATION: Primer WRB 1535 SGT3 F820 - Sgt3 3-prime
      Forward <210> SEQ ID NO 7
<211> LENGTH: 19
<212> TYPE: DNA
<213> ORGANISM: Artificial
<220> FEATURE:
<223> OTHER INFORMATION: Primer WRB 1526 PCR gt11 Rev - M13 Reverse Vector

<400> SEQUENCE: 7
aagggtggca tataggtcc                                          19

<210> SEQ ID NO 8
<211> LENGTH: 20
<212> TYPE: DNA
<213> ORGANISM: Artificial
<220> FEATURE:
<223> OTHER INFORMATION: Primer WRB 1526 PCR gt11 Rev - M13 Reverse Vector

<400> SEQUENCE: 8
aactggtaat ggtagcgacc                                         20

<210> SEQ ID NO 9
<211> LENGTH: 28
<212> TYPE: DNA
<213> ORGANISM: Artificial
<220> FEATURE:
<223> OTHER INFORMATION: primer WRB 1620 - Sgt3 5' KpnI Kozak

<400> SEQUENCE: 9
ggtaccatgg cgatggaaca gaatgaag                                28

<210> SEQ ID NO 10
<211> LENGTH: 31
<212> TYPE: DNA
<213> ORGANISM: Artificial
<220> FEATURE:
<223> OTHER INFORMATION: Primer WRB 1621 - Sgt3 3' KpnI native stop

<400> SEQUENCE: 10
ggtacctaaa aggatttctt gaaagcacaa c                            31

<210> SEQ ID NO 11
<211> LENGTH: 29
<212> TYPE: DNA
<213> ORGANISM: Artificial
<220> FEATURE:
<223> OTHER INFORMATION: Primer WRB 1624 Sgt3 3' XhoI read through fusion

<400> SEQUENCE: 11
ctcgagaaag gatttcttga aagcacaac                               29

<210> SEQ ID NO 12
<211> LENGTH: 1541
<212> TYPE: DNA
<213> ORGANISM: Solanum tuberosum Sgt3 K9
<220> FEATURE:
<221> NAME/KEY: CDS
<222> LOCATION: (7)..(1521)

<400> SEQUENCE: 12

```
ggtacc atg gcg atg gaa cag aat gaa gaa act gca atg ccg cat gtt         48
       Met Ala Met Glu Gln Asn Glu Glu Thr Ala Met Pro His Val
        1               5                  10 gtg ttc ata cca tac gcc atg acg agt cat ata act cca ttg gta cat        96
Val Phe Ile Pro Tyr Ala Met Thr Ser His Ile Thr Pro Leu Val His
 15              20                  25                  30 att gct aga ctc ttc gcc ctc cat ggc ctc aaa gtt act atc att gcc       144
Ile Ala Arg Leu Phe Ala Leu His Gly Leu Lys Val Thr Ile Ile Ala
                 35                  40                  45 cct cag cat aat gct ctt ctt ttt cag tcc tct gtc gat aga gac cgt       192
Pro Gln His Asn Ala Leu Leu Phe Gln Ser Ser Val Asp Arg Asp Arg
```

-continued

|  |  |  |  |  |  |  |  |  |  |  |  |  |  |  |  |
|---|---|---|---|---|---|---|---|---|---|---|---|---|---|---|---|
|  |  | 50 |  |  |  | 55 |  |  |  | 60 |  |  |  |  |  |

```
ctc ttt tcg ggc agc aat att act gtc cgg aca att caa ttt ccg tct      240
Leu Phe Ser Gly Ser Asn Ile Thr Val Arg Thr Ile Gln Phe Pro Ser
        65                  70                  75 gag gaa gtt gga tta cct gta gga att gaa aac ttc atc gca agc cct      288
Glu Glu Val Gly Leu Pro Val Gly Ile Glu Asn Phe Ile Ala Ser Pro
 80                  85                  90 tct atg gaa ata gtt ggc aaa gtt cac tat ggg ttt att ctg ctc caa      336
Ser Met Glu Ile Val Gly Lys Val His Tyr Gly Phe Ile Leu Leu Gln
 95                 100                 105                 110 aag att atg gag caa cta att cgg gag atc aat cca aac tgc att gtt      384
Lys Ile Met Glu Gln Leu Ile Arg Glu Ile Asn Pro Asn Cys Ile Val
               115                 120                 125 tcc gat atg ttc ttc cct tgg act gtt gat tta gct gag gag atg caa      432
Ser Asp Met Phe Phe Pro Trp Thr Val Asp Leu Ala Glu Glu Met Gln
       130                 135                 140 att ccg aga ttt tct ttt caa cca gcc act tcc ata cat caa tgt gct      480
Ile Pro Arg Phe Ser Phe Gln Pro Ala Thr Ser Ile His Gln Cys Ala
           145                 150                 155 tgg gtt ttc atc agg gaa ttt aaa cct tac aag aat gtg gcg tcg gat      528
Trp Val Phe Ile Arg Glu Phe Lys Pro Tyr Lys Asn Val Ala Ser Asp
       160                 165                 170 gct gaa aag ttt ttg att cct ggt ttg cct ctc gac atc aaa atg aaa      576
Ala Glu Lys Phe Leu Ile Pro Gly Leu Pro Leu Asp Ile Lys Met Lys
175                 180                 185                 190 gtc tca gag att gaa gat ttt ctt aaa gag gaa act gag tac aca aag      624
Val Ser Glu Ile Glu Asp Phe Leu Lys Glu Glu Thr Glu Tyr Thr Lys
                195                 200                 205 aca gta gat gac gtt tta caa gct gag gtt cgt agc cat ggt att att      672
Thr Val Asp Asp Val Leu Gln Ala Glu Val Arg Ser His Gly Ile Ile
           210                 215                 220 cat aac act tgc tct gag ctg gaa cct ggc gtt gcc caa ctc tac gaa      720
His Asn Thr Cys Ser Glu Leu Glu Pro Gly Val Ala Gln Leu Tyr Glu
       225                 230                 235 aaa gct aga gga gta aaa ggg tgg cat ata ggt cca ctt gct ctg ttt      768
Lys Ala Arg Gly Val Lys Gly Trp His Ile Gly Pro Leu Ala Leu Phe
   240                 245                 250 atc aac aaa tat gag gcg gaa att agt tct aaa caa att tcc aat tcg      816
Ile Asn Lys Tyr Glu Ala Glu Ile Ser Ser Lys Gln Ile Ser Asn Ser
255                 260                 265                 270 aat att aat tca tgt tct gac cct tgg aaa ggg tac ggt gat tgt ttc      864
Asn Ile Asn Ser Cys Ser Asp Pro Trp Lys Gly Tyr Gly Asp Cys Phe
                275                 280                 285 aat tgg ctt gaa aat caa caa cct aac tcc gtt ctc ttt gtt tgc ttt      912
Asn Trp Leu Glu Asn Gln Gln Pro Asn Ser Val Leu Phe Val Cys Phe
           290                 295                 300 gga agc atg ata aga ttt tcc gat gat cag ctt aag gaa atg gct gtt      960
Gly Ser Met Ile Arg Phe Ser Asp Asp Gln Leu Lys Glu Met Ala Val
       305                 310                 315 gga ttg aag gct gcc aac tgt cca act att tgg gtt ttt agg gag cag     1008
Gly Leu Lys Ala Ala Asn Cys Pro Thr Ile Trp Val Phe Arg Glu Gln
   320                 325                 330 gac aaa aat gaa gta gac gag aaa gat gag cat tct gac tgg agc cgt     1056
Asp Lys Asn Glu Val Asp Glu Lys Asp Glu His Ser Asp Trp Ser Arg
335                 340                 345                 350 aat ggt ttc aaa gaa atg gtt ggg gaa aag atg ttt atc atc caa ggc     1104
Asn Gly Phe Lys Glu Met Val Gly Glu Lys Met Phe Ile Ile Gln Gly
                355                 360                 365 tgg gca cca caa caa tta atc ctg aaa cat caa gca att ggt gga ttc     1152
```

-continued

```
Trp Ala Pro Gln Gln Leu Ile Leu Lys His Gln Ala Ile Gly Gly Phe
            370                 375                 380 tta act cat tgt ggt tgg aac tct ata ctt gag tct cta gcc gta ggt      1200
Leu Thr His Cys Gly Trp Asn Ser Ile Leu Glu Ser Leu Ala Val Gly
        385                 390                 395 gtt cca ttg atc aca tgg cca ctt ttc tca gac aac ttc tat acc gac      1248
Val Pro Leu Ile Thr Trp Pro Leu Phe Ser Asp Asn Phe Tyr Thr Asp
400                 405                 410 aag ctt ttg gag aca ctt ggc ctt gct att gga att gga gca gat gtg      1296
Lys Leu Leu Glu Thr Leu Gly Leu Ala Ile Gly Ile Gly Ala Asp Val
415                 420                 425                 430 tgg aat ccg ggg ttt ata tta tcg tgt cca ccc ctt tca gga gag aag      1344
Trp Asn Pro Gly Phe Ile Leu Ser Cys Pro Pro Leu Ser Gly Glu Lys
                435                 440                 445 ata gag ttg gcc gtc aag cgt tta atg aat aat tca gag gaa agt aga      1392
Ile Glu Leu Ala Val Lys Arg Leu Met Asn Asn Ser Glu Glu Ser Arg
            450                 455                 460 aaa att aga gaa aat gca aag ttg atg gca aag aag ctc aaa agt gcc      1440
Lys Ile Arg Glu Asn Ala Lys Leu Met Ala Lys Lys Leu Lys Ser Ala
        465                 470                 475 act gaa gaa ggt ggt tcc tct cat tcg cag ctt atc ggg tta att gag      1488
Thr Glu Glu Gly Gly Ser Ser His Ser Gln Leu Ile Gly Leu Ile Glu
480                 485                 490 gag atc aag cgt tgt gct ttc gag aaa tcc ttt taggtaccga gctcggatcc    1541
Glu Ile Lys Arg Cys Ala Phe Glu Lys Ser Phe
495                 500                 505

<210> SEQ ID NO 13
<211> LENGTH: 505
<212> TYPE: PRT
<213> ORGANISM: Solanum tuberosum Sgt3 K9

<400> SEQUENCE: 13

Met Ala Met Glu Gln Asn Glu Glu Thr Ala Met Pro His Val Val Phe
1               5                   10                  15

Ile Pro Tyr Ala Met Thr Ser His Ile Thr Pro Leu Val His Ile Ala
            20                  25                  30

Arg Leu Phe Ala Leu His Gly Leu Lys Val Thr Ile Ile Ala Pro Gln
        35                  40                  45

His Asn Ala Leu Leu Phe Gln Ser Ser Val Asp Arg Asp Arg Leu Phe
    50                  55                  60

Ser Gly Ser Asn Ile Thr Val Arg Thr Ile Gln Phe Pro Ser Glu Glu
65                  70                  75                  80

Val Gly Leu Pro Val Gly Ile Glu Asn Phe Ile Ala Ser Pro Ser Met
                85                  90                  95

Glu Ile Val Gly Lys Val His Tyr Gly Phe Ile Leu Leu Gln Lys Ile
            100                 105                 110

Met Glu Gln Leu Ile Arg Glu Ile Asn Pro Asn Cys Ile Val Ser Asp
        115                 120                 125

Met Phe Phe Pro Trp Thr Val Asp Leu Ala Glu Glu Met Gln Ile Pro
    130                 135                 140

Arg Phe Ser Phe Gln Pro Ala Thr Ser Ile His Gln Cys Ala Trp Val
145                 150                 155                 160

Phe Ile Arg Glu Phe Lys Pro Tyr Lys Asn Val Ala Ser Asp Ala Glu
                165                 170                 175

Lys Phe Leu Ile Pro Gly Leu Pro Leu Asp Ile Lys Met Lys Val Ser
            180                 185                 190
```

```
Glu Ile Glu Asp Phe Leu Lys Glu Glu Thr Glu Tyr Thr Lys Thr Val
        195                 200                 205

Asp Asp Val Leu Gln Ala Glu Val Arg Ser His Gly Ile Ile His Asn
        210                 215                 220

Thr Cys Ser Glu Leu Glu Pro Gly Val Ala Gln Leu Tyr Glu Lys Ala
225                 230                 235                 240

Arg Gly Val Lys Gly Trp His Ile Gly Pro Leu Ala Leu Phe Ile Asn
        245                 250                 255

Lys Tyr Glu Ala Glu Ile Ser Ser Lys Gln Ile Ser Asn Ser Asn Ile
        260                 265                 270

Asn Ser Cys Ser Asp Pro Trp Lys Gly Tyr Gly Asp Cys Phe Asn Trp
        275                 280                 285

Leu Glu Asn Gln Gln Pro Asn Ser Val Leu Phe Val Cys Phe Gly Ser
        290                 295                 300

Met Ile Arg Phe Ser Asp Asp Gln Leu Lys Glu Met Ala Val Gly Leu
305                 310                 315                 320

Lys Ala Ala Asn Cys Pro Thr Ile Trp Val Phe Arg Glu Gln Asp Lys
        325                 330                 335

Asn Glu Val Asp Glu Lys Asp Glu His Ser Asp Trp Ser Arg Asn Gly
        340                 345                 350

Phe Lys Glu Met Val Gly Glu Lys Met Phe Ile Ile Gln Gly Trp Ala
        355                 360                 365

Pro Gln Gln Leu Ile Leu Lys His Gln Ala Ile Gly Gly Phe Leu Thr
        370                 375                 380

His Cys Gly Trp Asn Ser Ile Leu Glu Ser Leu Ala Val Gly Val Pro
385                 390                 395                 400

Leu Ile Thr Trp Pro Leu Phe Ser Asp Asn Phe Tyr Thr Asp Lys Leu
        405                 410                 415

Leu Glu Thr Leu Gly Leu Ala Ile Gly Ile Gly Ala Asp Val Trp Asn
        420                 425                 430

Pro Gly Phe Ile Leu Ser Cys Pro Pro Leu Ser Gly Glu Lys Ile Glu
        435                 440                 445

Leu Ala Val Lys Arg Leu Met Asn Asn Ser Glu Ser Arg Lys Ile
        450                 455                 460

Arg Glu Asn Ala Lys Leu Met Ala Lys Leu Lys Ser Ala Thr Glu
465                 470                 475                 480

Glu Gly Gly Ser Ser His Ser Gln Leu Ile Gly Leu Ile Glu Glu Ile
        485                 490                 495

Lys Arg Cys Ala Phe Glu Lys Ser Phe
        500                 505

<210> SEQ ID NO 14
<211> LENGTH: 1527
<212> TYPE: DNA
<213> ORGANISM: Solanum tuberosum Sgt3 KX9
<220> FEATURE:
<221> NAME/KEY: CDS
<222> LOCATION: (7)..(1521)

<400> SEQUENCE: 14 ggtacc atg gcg atg gaa cag aat gaa gaa act gca atg ccg cat gtt     48
       Met Ala Met Glu Gln Asn Glu Glu Thr Ala Met Pro His Val
         1               5                  10 gtg ttc ata cca tac gcc atg acg agt cat ata act cca ttg gta cat   96
Val Phe Ile Pro Tyr Ala Met Thr Ser His Ile Thr Pro Leu Val His
 15                  20                  25                  30
```

-continued

| | |
|---|---|
| att gct aga ctc ttc gcc ctc cat ggc ctc aaa gtt act atc att gcc<br>Ile Ala Arg Leu Phe Ala Leu His Gly Leu Lys Val Thr Ile Ile Ala<br>35 40 45 | 144 |
| cct cag cat aat gct ctt ctt ttt cag tcc tct gtc gat aga gac cgt<br>Pro Gln His Asn Ala Leu Leu Phe Gln Ser Ser Val Asp Arg Asp Arg<br>50 55 60 | 192 |
| ctc ttt tcg ggc agc aat att act gtc cgg aca att caa ttt ccg tct<br>Leu Phe Ser Gly Ser Asn Ile Thr Val Arg Thr Ile Gln Phe Pro Ser<br>65 70 75 | 240 |
| gag gaa gtt gga tta cct gta gga att gaa aac ttc atc gca agc cct<br>Glu Glu Val Gly Leu Pro Val Gly Ile Glu Asn Phe Ile Ala Ser Pro<br>80 85 90 | 288 |
| tct atg gaa ata gtt ggc aaa gtt cac tat ggg ttt att ctg ctc caa<br>Ser Met Glu Ile Val Gly Lys Val His Tyr Gly Phe Ile Leu Leu Gln<br>95 100 105 110 | 336 |
| aag att atg gag caa cta att cgg gag atc aat cca aac tgc att gtt<br>Lys Ile Met Glu Gln Leu Ile Arg Glu Ile Asn Pro Asn Cys Ile Val<br>115 120 125 | 384 |
| tcc gat atg ttc ttc cct tgg act gtt gat tta gct gag gag atg caa<br>Ser Asp Met Phe Phe Pro Trp Thr Val Asp Leu Ala Glu Glu Met Gln<br>130 135 140 | 432 |
| att ccg aga ttt tct ttt caa cca gcc act tcc ata cat caa tgt gct<br>Ile Pro Arg Phe Ser Phe Gln Pro Ala Thr Ser Ile His Gln Cys Ala<br>145 150 155 | 480 |
| tgg gtt ttc atc agg gaa ttt aaa cct tac aag aat gtg gcg tcg gat<br>Trp Val Phe Ile Arg Glu Phe Lys Pro Tyr Lys Asn Val Ala Ser Asp<br>160 165 170 | 528 |
| gct gaa aag ttt ttg att cct ggt ttg cct ctc gac atc aaa atg aaa<br>Ala Glu Lys Phe Leu Ile Pro Gly Leu Pro Leu Asp Ile Lys Met Lys<br>175 180 185 190 | 576 |
| gtc tca gag att gaa gat ttt ctt aaa gag gaa act gag tac aca aag<br>Val Ser Glu Ile Glu Asp Phe Leu Lys Glu Glu Thr Glu Tyr Thr Lys<br>195 200 205 | 624 |
| aca gta gat gac gtt tta caa gct gag gtt cgt agc cat ggt att att<br>Thr Val Asp Asp Val Leu Gln Ala Glu Val Arg Ser His Gly Ile Ile<br>210 215 220 | 672 |
| cat aac act tgc tct gag ctg gaa cct ggc gtt gcc caa ctc tac gaa<br>His Asn Thr Cys Ser Glu Leu Glu Pro Gly Val Ala Gln Leu Tyr Glu<br>225 230 235 | 720 |
| aaa gct aga gga gta aaa ggg tgg cat ata ggt cca ctt gct ctg ttt<br>Lys Ala Arg Gly Val Lys Gly Trp His Ile Gly Pro Leu Ala Leu Phe<br>240 245 250 | 768 |
| atc aac aaa tat gaa gcg gaa att agt tct aaa caa att tcc aat tcg<br>Ile Asn Lys Tyr Glu Ala Glu Ile Ser Ser Lys Gln Ile Ser Asn Ser<br>255 260 265 270 | 816 |
| aat att aat tca tgt tct gac cct tgg aaa ggg tac ggt gat tgt ttc<br>Asn Ile Asn Ser Cys Ser Asp Pro Trp Lys Gly Tyr Gly Asp Cys Phe<br>275 280 285 | 864 |
| aat tgg ctt gaa aat caa caa cct aac tcc gtt ctc ttt gtt tgc ttt<br>Asn Trp Leu Glu Asn Gln Gln Pro Asn Ser Val Leu Phe Val Cys Phe<br>290 295 300 | 912 |
| gga agc atg ata aga ttt tcc gat gat cag ctt aag gaa atg gct gtt<br>Gly Ser Met Ile Arg Phe Ser Asp Asp Gln Leu Lys Glu Met Ala Val<br>305 310 315 | 960 |
| gga ttg aag gct gcc aac tgt cca act att tgg gtt ttt agg gag cag<br>Gly Leu Lys Ala Ala Asn Cys Pro Thr Ile Trp Val Phe Arg Glu Gln<br>320 325 330 | 1008 |
| gac aaa aat gaa gta gac gag aaa gat gag cat tct gac tgg agc cgt<br>Asp Lys Asn Glu Val Asp Glu Lys Asp Glu His Ser Asp Trp Ser Arg<br>335 340 345 350 | 1056 |

```
aat ggt ttc aaa gaa atg att ggg gaa aag atg ttt atc atc caa ggc     1104
Asn Gly Phe Lys Glu Met Ile Gly Glu Lys Met Phe Ile Ile Gln Gly
            355                 360                 365 tgg gca cca caa caa tta atc ctg aaa cat caa gca att ggt gga ttc     1152
Trp Ala Pro Gln Gln Leu Ile Leu Lys His Gln Ala Ile Gly Gly Phe
        370                 375                 380 tta act cat tgt ggt tgg aac tct ata ctt gag tct cta gcc gta ggt     1200
Leu Thr His Cys Gly Trp Asn Ser Ile Leu Glu Ser Leu Ala Val Gly
    385                 390                 395 gtt cca ttg atc aca tgg cca ctt ttc tca gac aac ttc tat acc gac     1248
Val Pro Leu Ile Thr Trp Pro Leu Phe Ser Asp Asn Phe Tyr Thr Asp
400                 405                 410 aag ctt ttg gag aca ctt ggc ctt gct att gga att gga gca gat gtg     1296
Lys Leu Leu Glu Thr Leu Gly Leu Ala Ile Gly Ile Gly Ala Asp Val
415                 420                 425                 430 tgg aat ccg ggg ttt ata tta tcg tgt cca ccc ctt tca gga gag aag     1344
Trp Asn Pro Gly Phe Ile Leu Ser Cys Pro Pro Leu Ser Gly Glu Lys
                435                 440                 445 ata gag ttg gcc gtc aag cgt tta atg aat aat tca gag gaa agt aga     1392
Ile Glu Leu Ala Val Lys Arg Leu Met Asn Asn Ser Glu Glu Ser Arg
            450                 455                 460 aaa att aga gaa aat gca aag ttg atg gca aag aag ctc aaa agt gcc     1440
Lys Ile Arg Glu Asn Ala Lys Leu Met Ala Lys Lys Leu Lys Ser Ala
        465                 470                 475 act gaa gaa ggt ggt tcc tct cat tca cag ctt atc ggg tta att gag     1488
Thr Glu Glu Gly Gly Ser Ser His Ser Gln Leu Ile Gly Leu Ile Glu
    480                 485                 490 gag atc aag cgt tgt gct ttc aag aaa tcc ttt ctcgag                  1527
Glu Ile Lys Arg Cys Ala Phe Lys Lys Ser Phe
495                 500                 505

<210> SEQ ID NO 15
<211> LENGTH: 505
<212> TYPE: PRT
<213> ORGANISM: Solanum tuberosum Sgt3 KX9

<400> SEQUENCE: 15

Met Ala Met Glu Gln Asn Glu Thr Ala Met Pro His Val Val Phe
1               5                   10                  15

Ile Pro Tyr Ala Met Thr Ser His Ile Thr Pro Leu Val His Ile Ala
                20                  25                  30

Arg Leu Phe Ala Leu His Gly Leu Lys Val Thr Ile Ile Ala Pro Gln
            35                  40                  45

His Asn Ala Leu Leu Phe Gln Ser Ser Val Asp Arg Asp Arg Leu Phe
        50                  55                  60

Ser Gly Ser Asn Ile Thr Val Arg Thr Ile Gln Phe Pro Ser Glu Glu
65                  70                  75                  80

Val Gly Leu Pro Val Gly Ile Glu Asn Phe Ile Ala Ser Pro Ser Met
                85                  90                  95

Glu Ile Val Gly Lys Val His Tyr Gly Phe Ile Leu Leu Gln Lys Ile
            100                 105                 110

Met Glu Gln Leu Ile Arg Glu Ile Asn Pro Asn Cys Ile Val Ser Asp
        115                 120                 125

Met Phe Phe Pro Trp Thr Val Asp Leu Ala Glu Glu Met Gln Ile Pro
    130                 135                 140

Arg Phe Ser Phe Gln Pro Ala Thr Ser Ile His Gln Cys Ala Trp Val
145                 150                 155                 160
```

```
Phe Ile Arg Glu Phe Lys Pro Tyr Lys Asn Val Ala Ser Asp Ala Glu
            165                 170                 175
Lys Phe Leu Ile Pro Gly Leu Pro Leu Asp Ile Lys Met Lys Val Ser
        180                 185                 190
Glu Ile Glu Asp Phe Leu Lys Glu Thr Tyr Thr Lys Thr Val
    195                 200                 205
Asp Asp Val Leu Gln Ala Glu Val Arg Ser His Gly Ile Ile His Asn
210                 215                 220
Thr Cys Ser Glu Leu Glu Pro Gly Val Ala Gln Leu Tyr Glu Lys Ala
225                 230                 235                 240
Arg Gly Val Lys Gly Trp His Ile Gly Pro Leu Ala Leu Phe Ile Asn
                245                 250                 255
Lys Tyr Glu Ala Glu Ile Ser Ser Lys Gln Ile Ser Asn Ser Asn Ile
            260                 265                 270
Asn Ser Cys Ser Asp Pro Trp Lys Gly Tyr Gly Asp Cys Phe Asn Trp
        275                 280                 285
Leu Glu Asn Gln Gln Pro Asn Ser Val Leu Phe Val Cys Phe Gly Ser
    290                 295                 300
Met Ile Arg Phe Ser Asp Asp Gln Leu Lys Glu Met Ala Val Gly Leu
305                 310                 315                 320
Lys Ala Ala Asn Cys Pro Thr Ile Trp Val Phe Arg Glu Gln Asp Lys
                325                 330                 335
Asn Glu Val Asp Glu Lys Asp Glu His Ser Asp Trp Ser Arg Asn Gly
            340                 345                 350
Phe Lys Glu Met Ile Gly Glu Lys Met Phe Ile Ile Gln Gly Trp Ala
        355                 360                 365
Pro Gln Gln Leu Ile Leu Lys His Gln Ala Ile Gly Gly Phe Leu Thr
    370                 375                 380
His Cys Gly Trp Asn Ser Ile Leu Glu Ser Leu Ala Val Gly Val Pro
385                 390                 395                 400
Leu Ile Thr Trp Pro Leu Phe Ser Asp Asn Phe Tyr Thr Asp Lys Leu
                405                 410                 415
Leu Glu Thr Leu Gly Leu Ala Ile Gly Ile Gly Ala Asp Val Trp Asn
            420                 425                 430
Pro Gly Phe Ile Leu Ser Cys Pro Pro Leu Ser Gly Glu Lys Ile Glu
        435                 440                 445
Leu Ala Val Lys Arg Leu Met Asn Asn Ser Glu Glu Ser Arg Lys Ile
    450                 455                 460
Arg Glu Asn Ala Lys Leu Met Ala Lys Lys Leu Lys Ser Ala Thr Glu
465                 470                 475                 480
Glu Gly Gly Ser Ser His Ser Gln Leu Ile Gly Leu Ile Glu Glu Ile
                485                 490                 495
Lys Arg Cys Ala Phe Lys Lys Ser Phe
            500                 505

<210> SEQ ID NO 16
<211> LENGTH: 1518
<212> TYPE: DNA
<213> ORGANISM: Solanum tuberosum Sgt3
<220> FEATURE:
<221> NAME/KEY: CDS
<222> LOCATION: (1)..(1518)

<400> SEQUENCE: 16 atg gcg atg gaa cag aat gaa gaa act gca atg ccg cat gtt gtg ttc    48
Met Ala Met Glu Gln Asn Glu Glu Thr Ala Met Pro His Val Val Phe
```

-continued

| | | | | | | | | | | | | | | | | |
|---|---|---|---|---|---|---|---|---|---|---|---|---|---|---|---|---|
| 1 | | | | 5 | | | | | 10 | | | | | 15 | | |

| | | | | | | | | | | | | | | | | |
|---|---|---|---|---|---|---|---|---|---|---|---|---|---|---|---|---|
| ata | cca | tac | gcc | atg | acg | agt | cat | ata | act | cca | ttg | gta | cat | att | gct | 96 |
| Ile | Pro | Tyr | Ala | Met | Thr | Ser | His | Ile | Thr | Pro | Leu | Val | His | Ile | Ala | |
| | | | | 20 | | | | | 25 | | | | | 30 | | |
| aga | ctc | ttc | gcc | ctc | cat | ggc | ctc | aaa | gtt | act | atc | att | gcc | cct | cag | 144 |
| Arg | Leu | Phe | Ala | Leu | His | Gly | Leu | Lys | Val | Thr | Ile | Ile | Ala | Pro | Gln | |
| | | | | 35 | | | | | 40 | | | | | 45 | | |
| cat | aat | gct | ctt | ctt | ttt | cag | tcc | tct | gtc | gat | aga | gac | cgt | ctc | ttt | 192 |
| His | Asn | Ala | Leu | Leu | Phe | Gln | Ser | Ser | Val | Asp | Arg | Asp | Arg | Leu | Phe | |
| | | | 50 | | | | | 55 | | | | | 60 | | | |
| tcg | ggc | agc | aat | att | act | gtc | cgg | aca | att | caa | ttt | ccg | tct | gag | gaa | 240 |
| Ser | Gly | Ser | Asn | Ile | Thr | Val | Arg | Thr | Ile | Gln | Phe | Pro | Ser | Glu | Glu | |
| 65 | | | | | 70 | | | | | 75 | | | | | 80 | |
| gtt | gga | tta | cct | gta | gga | att | gaa | aac | ttc | atc | gca | agc | cct | tct | atg | 288 |
| Val | Gly | Leu | Pro | Val | Gly | Ile | Glu | Asn | Phe | Ile | Ala | Ser | Pro | Ser | Met | |
| | | | | | 85 | | | | | 90 | | | | | 95 | |
| gaa | ata | gtt | ggc | aaa | gtt | cac | tat | ggg | ttt | att | ctg | ctc | caa | aag | att | 336 |
| Glu | Ile | Val | Gly | Lys | Val | His | Tyr | Gly | Phe | Ile | Leu | Leu | Gln | Lys | Ile | |
| | | | | 100 | | | | | 105 | | | | | 110 | | |
| atg | gag | caa | cta | att | cgg | gag | atc | aat | cca | aac | tgc | att | gtt | tcc | gat | 384 |
| Met | Glu | Gln | Leu | Ile | Arg | Glu | Ile | Asn | Pro | Asn | Cys | Ile | Val | Ser | Asp | |
| | | | | 115 | | | | | 120 | | | | | 125 | | |
| atg | ttc | ttc | cct | tgg | act | gtt | gat | tta | gct | gag | gag | atg | caa | att | ccg | 432 |
| Met | Phe | Phe | Pro | Trp | Thr | Val | Asp | Leu | Ala | Glu | Glu | Met | Gln | Ile | Pro | |
| | | | 130 | | | | | 135 | | | | | 140 | | | |
| aga | ttt | tct | ttt | caa | cca | gcc | act | tcc | ata | cat | caa | tgt | gct | tgg | gtt | 480 |
| Arg | Phe | Ser | Phe | Gln | Pro | Ala | Thr | Ser | Ile | His | Gln | Cys | Ala | Trp | Val | |
| 145 | | | | | 150 | | | | | 155 | | | | | 160 | |
| ttc | atc | agg | gaa | ttt | aaa | cct | tac | aag | aat | gtg | gcg | tcg | gat | gct | gaa | 528 |
| Phe | Ile | Arg | Glu | Phe | Lys | Pro | Tyr | Lys | Asn | Val | Ala | Ser | Asp | Ala | Glu | |
| | | | | | 165 | | | | | 170 | | | | | 175 | |
| aag | ttt | ttg | att | cct | ggt | tgc | cct | ctc | gac | atc | aaa | atg | aaa | gtc | tca | 576 |
| Lys | Phe | Leu | Ile | Pro | Gly | Leu | Pro | Leu | Asp | Ile | Lys | Met | Lys | Val | Ser | |
| | | | | 180 | | | | | 185 | | | | | 190 | | |
| gag | att | gaa | gat | ttt | ctt | aaa | gag | gaa | act | gag | tac | aca | aag | aca | gta | 624 |
| Glu | Ile | Glu | Asp | Phe | Leu | Lys | Glu | Glu | Thr | Glu | Tyr | Thr | Lys | Thr | Val | |
| | | | | 195 | | | | | 200 | | | | | 205 | | |
| gat | gac | gtt | tta | caa | gct | gag | gtt | cgt | agc | cat | ggt | att | att | cat | aac | 672 |
| Asp | Asp | Val | Leu | Gln | Ala | Glu | Val | Arg | Ser | His | Gly | Ile | Ile | His | Asn | |
| | | | 210 | | | | | 215 | | | | | 220 | | | |
| act | tgc | tct | gag | ctg | gaa | cct | ggc | gtt | gcc | caa | ctc | tac | gaa | aaa | gct | 720 |
| Thr | Cys | Ser | Glu | Leu | Glu | Pro | Gly | Val | Ala | Gln | Leu | Tyr | Glu | Lys | Ala | |
| 225 | | | | | 230 | | | | | 235 | | | | | 240 | |
| aga | gga | gta | aaa | ggg | tgg | cat | ata | ggt | cca | ctt | gct | ctg | ttt | atc | aac | 768 |
| Arg | Gly | Val | Lys | Gly | Trp | His | Ile | Gly | Pro | Leu | Ala | Leu | Phe | Ile | Asn | |
| | | | | | 245 | | | | | 250 | | | | | 255 | |
| aaa | tat | gaa | gcg | gaa | att | agt | tct | aaa | caa | att | tcc | aat | tcg | aat | att | 816 |
| Lys | Tyr | Glu | Ala | Glu | Ile | Ser | Ser | Lys | Gln | Ile | Ser | Asn | Ser | Asn | Ile | |
| | | | | 260 | | | | | 265 | | | | | 270 | | |
| aat | tca | tgt | tct | gac | cct | tgg | aaa | ggg | tac | ggt | gat | tgt | ttc | aat | tgg | 864 |
| Asn | Ser | Cys | Ser | Asp | Pro | Trp | Lys | Gly | Tyr | Gly | Asp | Cys | Phe | Asn | Trp | |
| | | | 275 | | | | | 280 | | | | | 285 | | | |
| ctt | gaa | aat | caa | caa | cct | aac | tcc | gtt | ctc | ttt | gtt | tgc | ttt | gga | agc | 912 |
| Leu | Glu | Asn | Gln | Gln | Pro | Asn | Ser | Val | Leu | Phe | Val | Cys | Phe | Gly | Ser | |
| | | | | 290 | | | | | 295 | | | | | 300 | | |
| atg | ata | aga | ttt | tcc | gat | gat | cag | ctt | aag | gaa | atg | gct | gtt | gga | ttg | 960 |
| Met | Ile | Arg | Phe | Ser | Asp | Asp | Gln | Leu | Lys | Glu | Met | Ala | Val | Gly | Leu | |
| 305 | | | | | 310 | | | | | 315 | | | | | 320 | |
| aag | gct | gcc | aac | tgt | cca | act | att | tgg | gtt | ttt | agg | gag | cag | gac | aaa | 1008 |

```
                Lys Ala Ala Asn Cys Pro Thr Ile Trp Val Phe Arg Glu Gln Asp Lys
                            325                 330                 335 aat gaa gta gac gag aaa gat gag cat tct gac tgg agc cgt aat ggt        1056
Asn Glu Val Asp Glu Lys Asp Glu His Ser Asp Trp Ser Arg Asn Gly
        340                 345                 350 ttc aaa gaa atg att ggg gaa aag atg ttt atc atc caa ggc tgg gca        1104
Phe Lys Glu Met Ile Gly Glu Lys Met Phe Ile Ile Gln Gly Trp Ala
    355                 360                 365 cca caa caa tta atc ctg aaa cat caa gca att ggt gga ttc tta act        1152
Pro Gln Gln Leu Ile Leu Lys His Gln Ala Ile Gly Gly Phe Leu Thr
370                 375                 380 cat tgt ggt tgg aac tct ata ctt gag tct cta gcc gta ggt gtt cca        1200
His Cys Gly Trp Asn Ser Ile Leu Glu Ser Leu Ala Val Gly Val Pro
385                 390                 395                 400 ttg atc aca tgg cca ctt ttc tca gac aac ttc tat acc gac aag ctt        1248
Leu Ile Thr Trp Pro Leu Phe Ser Asp Asn Phe Tyr Thr Asp Lys Leu
            405                 410                 415 ttg gag aca ctt ggc ctt gct att gga att gga gca gat gtg tgg aat        1296
Leu Glu Thr Leu Gly Leu Ala Ile Gly Ile Gly Ala Asp Val Trp Asn
        420                 425                 430 ccg ggg ttt ata tta tcg tgt cca ccc ctt tca gga gag aag ata gag        1344
Pro Gly Phe Ile Leu Ser Cys Pro Pro Leu Ser Gly Glu Lys Ile Glu
    435                 440                 445 ttg gcc gtc aag cgt tta atg aat aat tca gag gaa agt aga aaa att        1392
Leu Ala Val Lys Arg Leu Met Asn Asn Ser Glu Glu Ser Arg Lys Ile
450                 455                 460 aga gaa aat gca aag ttg atg gca aag aag ctc aaa agt gcc act gaa        1440
Arg Glu Asn Ala Lys Leu Met Ala Lys Lys Leu Lys Ser Ala Thr Glu
465                 470                 475                 480 gaa ggt ggt tcc tct cat tca cag ctt atc ggg tta att gag gag atc        1488
Glu Gly Gly Ser Ser His Ser Gln Leu Ile Gly Leu Ile Glu Glu Ile
            485                 490                 495 aag cgt tgt gct ttc aag aaa tcc ttt tag                                1518
Lys Arg Cys Ala Phe Lys Lys Ser Phe
        500                 505

<210> SEQ ID NO 17
<211> LENGTH: 505
<212> TYPE: PRT
<213> ORGANISM: Solanum tuberosum Sgt3

<400> SEQUENCE: 17

Met Ala Met Glu Gln Asn Glu Glu Thr Ala Met Pro His Val Val Phe
1               5                   10                  15

Ile Pro Tyr Ala Met Thr Ser His Ile Thr Pro Leu Val His Ile Ala
            20                  25                  30

Arg Leu Phe Ala Leu His Gly Leu Lys Val Thr Ile Ile Ala Pro Gln
        35                  40                  45

His Asn Ala Leu Leu Phe Gln Ser Ser Val Asp Arg Asp Arg Leu Phe
    50                  55                  60

Ser Gly Ser Asn Ile Thr Val Arg Thr Ile Gln Phe Pro Ser Glu Glu
65                  70                  75                  80

Val Gly Leu Pro Val Gly Ile Glu Asn Phe Ile Ala Ser Pro Ser Met
            85                  90                  95

Glu Ile Val Gly Lys Val His Tyr Gly Phe Ile Leu Leu Gln Lys Ile
        100                 105                 110

Met Glu Gln Leu Ile Arg Glu Ile Asn Pro Asn Cys Ile Val Ser Asp
    115                 120                 125
```

```
Met Phe Phe Pro Trp Thr Val Asp Leu Ala Glu Glu Met Gln Ile Pro
130                 135                 140

Arg Phe Ser Phe Gln Pro Ala Thr Ser Ile His Gln Cys Ala Trp Val
145                 150                 155                 160

Phe Ile Arg Glu Phe Lys Pro Tyr Lys Asn Val Ala Ser Asp Ala Glu
                165                 170                 175

Lys Phe Leu Ile Pro Gly Leu Pro Leu Asp Ile Lys Met Lys Val Ser
            180                 185                 190

Glu Ile Glu Asp Phe Leu Lys Glu Glu Thr Glu Tyr Thr Lys Thr Val
        195                 200                 205

Asp Asp Val Leu Gln Ala Glu Val Arg Ser His Gly Ile Ile His Asn
210                 215                 220

Thr Cys Ser Glu Leu Glu Pro Gly Val Ala Gln Leu Tyr Glu Lys Ala
225                 230                 235                 240

Arg Gly Val Lys Gly Trp His Ile Gly Pro Leu Ala Leu Phe Ile Asn
                245                 250                 255

Lys Tyr Glu Ala Glu Ile Ser Ser Lys Gln Ile Ser Asn Ser Asn Ile
            260                 265                 270

Asn Ser Cys Ser Asp Pro Trp Lys Gly Tyr Gly Asp Cys Phe Asn Trp
        275                 280                 285

Leu Glu Asn Gln Gln Pro Asn Ser Val Leu Phe Val Cys Phe Gly Ser
290                 295                 300

Met Ile Arg Phe Ser Asp Asp Gln Leu Lys Glu Met Ala Val Gly Leu
305                 310                 315                 320

Lys Ala Ala Asn Cys Pro Thr Ile Trp Val Phe Arg Glu Gln Asp Lys
                325                 330                 335

Asn Glu Val Asp Glu Lys Asp Glu His Ser Asp Trp Ser Arg Asn Gly
            340                 345                 350

Phe Lys Glu Met Ile Gly Glu Lys Met Phe Ile Ile Gln Gly Trp Ala
        355                 360                 365

Pro Gln Gln Leu Ile Leu Lys His Gln Ala Ile Gly Gly Phe Leu Thr
370                 375                 380

His Cys Gly Trp Asn Ser Ile Leu Glu Ser Leu Ala Val Gly Val Pro
385                 390                 395                 400

Leu Ile Thr Trp Pro Leu Phe Ser Asp Asn Phe Tyr Thr Asp Lys Leu
                405                 410                 415

Leu Glu Thr Leu Gly Leu Ala Ile Gly Ile Gly Ala Asp Val Trp Asn
            420                 425                 430

Pro Gly Phe Ile Leu Ser Cys Pro Pro Leu Ser Gly Glu Lys Ile Glu
        435                 440                 445

Leu Ala Val Lys Arg Leu Met Asn Asn Ser Glu Ser Arg Lys Ile
450                 455                 460

Arg Glu Asn Ala Lys Leu Met Ala Lys Leu Lys Ser Ala Thr Glu
465                 470                 475                 480

Glu Gly Gly Ser Ser His Ser Gln Leu Ile Gly Leu Ile Glu Glu Ile
                485                 490                 495

Lys Arg Cys Ala Phe Lys Lys Ser Phe
            500                 505

<210> SEQ ID NO 18
<211> LENGTH: 1467
<212> TYPE: DNA
<213> ORGANISM: Solanum tuberosum Sgt1
<220> FEATURE:
<221> NAME/KEY: CDS
```

<222> LOCATION: (1)..(1467)

<400> SEQUENCE: 18

| | | | | | | | | | | | | | | | | |
|---|---|---|---|---|---|---|---|---|---|---|---|---|---|---|---|---|
| atg | gta | gca | acc | tgc | aac | agt | ggc | gaa | atc | ctc | cat | gtt | ctt | ttc | ctt | 48 |
| Met | Val | Ala | Thr | Cys | Asn | Ser | Gly | Glu | Ile | Leu | His | Val | Leu | Phe | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccc | ttc | tta | tcc | gct | ggt | cat | ttc | atc | cca | tta | gtt | aac | gcc | gca | agg | 96 |
| Pro | Phe | Leu | Ser | Ala | Gly | His | Phe | Ile | Pro | Leu | Val | Asn | Ala | Ala | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| cta | ttc | gcc | tcc | cgc | ggt | gtt | aaa | gcc | aca | atc | ctc | act | acc | cct | cat | 144 |
| Leu | Phe | Ala | Ser | Arg | Gly | Val | Lys | Ala | Thr | Ile | Leu | Thr | Thr | Pro | His | |
| | | 35 | | | | | 40 | | | | | 45 | | | | |

| | | | | | | | | | | | | | | | | |
|---|---|---|---|---|---|---|---|---|---|---|---|---|---|---|---|---|
| aat | gcc | tta | ctt | ttt | aga | tct | act | att | gac | gat | gat | gtt | cga | att | tcc | 192 |
| Asn | Ala | Leu | Leu | Phe | Arg | Ser | Thr | Ile | Asp | Asp | Asp | Val | Arg | Ile | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| gga | ttt | ccc | att | tct | atc | gta | act | att | aaa | ttc | ccc | tct | gct | gaa | gtt | 240 |
| Gly | Phe | Pro | Ile | Ser | Ile | Val | Thr | Ile | Lys | Phe | Pro | Ser | Ala | Glu | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggg | ttg | cct | gaa | gga | att | gag | agc | ttt | aac | tct | gcc | act | tca | cct | gaa | 288 |
| Gly | Leu | Pro | Glu | Gly | Ile | Glu | Ser | Phe | Asn | Ser | Ala | Thr | Ser | Pro | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| atg | cct | cat | aaa | att | ttt | tat | gct | ctt | tct | ctt | cta | caa | aag | cca | atg | 336 |
| Met | Pro | His | Lys | Ile | Phe | Tyr | Ala | Leu | Ser | Leu | Leu | Gln | Lys | Pro | Met | |
| | | | 100 | | | | | 105 | | | | | 110 | | | |

| | | | | | | | | | | | | | | | | |
|---|---|---|---|---|---|---|---|---|---|---|---|---|---|---|---|---|
| gaa | gat | aaa | att | cgt | gaa | ctc | cgt | cct | gat | tgc | att | ttt | tct | gat | atg | 384 |
| Glu | Asp | Lys | Ile | Arg | Glu | Leu | Arg | Pro | Asp | Cys | Ile | Phe | Ser | Asp | Met | |
| | | 115 | | | | | 120 | | | | | 125 | | | | |

| | | | | | | | | | | | | | | | | |
|---|---|---|---|---|---|---|---|---|---|---|---|---|---|---|---|---|
| tac | ttc | cct | tgg | aca | gta | gat | att | gct | gat | gag | ctt | cac | atc | cct | cgt | 432 |
| Tyr | Phe | Pro | Trp | Thr | Val | Asp | Ile | Ala | Asp | Glu | Leu | His | Ile | Pro | Arg | |
| | 130 | | | | | 135 | | | | | 140 | | | | | |

| | | | | | | | | | | | | | | | | |
|---|---|---|---|---|---|---|---|---|---|---|---|---|---|---|---|---|
| att | ttg | tac | aat | ttg | tct | gct | tac | atg | tgc | tac | agc | att | atg | cac | aac | 480 |
| Ile | Leu | Tyr | Asn | Leu | Ser | Ala | Tyr | Met | Cys | Tyr | Ser | Ile | Met | His | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctt | aag | gtt | tac | aga | cct | cac | aag | cag | cct | aat | cta | gac | gaa | tct | caa | 528 |
| Leu | Lys | Val | Tyr | Arg | Pro | His | Lys | Gln | Pro | Asn | Leu | Asp | Glu | Ser | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| agt | ttc | gtg | gtt | cct | ggt | tta | cct | gat | gag | ata | aag | ttc | aag | tta | tcc | 576 |
| Ser | Phe | Val | Val | Pro | Gly | Leu | Pro | Asp | Glu | Ile | Lys | Phe | Lys | Leu | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| caa | ctg | aca | gat | gat | ctg | aga | aag | tcg | gat | gac | caa | aag | act | gtt | ttt | 624 |
| Gln | Leu | Thr | Asp | Asp | Leu | Arg | Lys | Ser | Asp | Asp | Gln | Lys | Thr | Val | Phe | |
| | | 195 | | | | | 200 | | | | | 205 | | | | |

| | | | | | | | | | | | | | | | | |
|---|---|---|---|---|---|---|---|---|---|---|---|---|---|---|---|---|
| gac | gaa | ttg | ctc | gaa | caa | gtt | gaa | gat | tcg | gag | gaa | cga | agc | tat | ggc | 672 |
| Asp | Glu | Leu | Leu | Glu | Gln | Val | Glu | Asp | Ser | Glu | Glu | Arg | Ser | Tyr | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| att | gtt | cat | gat | aca | ttt | tat | gag | cta | gaa | cct | gca | tat | gtt | gac | tac | 720 |
| Ile | Val | His | Asp | Thr | Phe | Tyr | Glu | Leu | Glu | Pro | Ala | Tyr | Val | Asp | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tac | cag | aaa | tta | aag | aaa | cca | aaa | tgt | tgg | cat | ttt | ggt | ccg | ctc | tct | 768 |
| Tyr | Gln | Lys | Leu | Lys | Lys | Pro | Lys | Cys | Trp | His | Phe | Gly | Pro | Leu | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| cat | ttt | gca | tcc | aaa | atc | cgt | agt | aag | gaa | cta | att | tct | gag | cat | aac | 816 |
| His | Phe | Ala | Ser | Lys | Ile | Arg | Ser | Lys | Glu | Leu | Ile | Ser | Glu | His | Asn | |
| | | | 260 | | | | | 265 | | | | | 270 | | | |

| | | | | | | | | | | | | | | | | |
|---|---|---|---|---|---|---|---|---|---|---|---|---|---|---|---|---|
| aac | aat | gag | att | gtt | ata | gat | tgg | ttg | aat | gca | cag | aaa | cct | aaa | tcg | 864 |
| Asn | Asn | Glu | Ile | Val | Ile | Asp | Trp | Leu | Asn | Ala | Gln | Lys | Pro | Lys | Ser | |
| | | 275 | | | | | 280 | | | | | 285 | | | | |

| | | | | | | | | | | | | | | | | |
|---|---|---|---|---|---|---|---|---|---|---|---|---|---|---|---|---|
| gtt | ctc | tat | gta | tct | ttc | gga | agc | atg | gct | aga | ttt | cct | gag | agc | caa | 912 |
| Val | Leu | Tyr | Val | Ser | Phe | Gly | Ser | Met | Ala | Arg | Phe | Pro | Glu | Ser | Gln | |
| | 290 | | | | | 295 | | | | | 300 | | | | | |

```
ctg aat gaa ata gcc caa gct ctg gat gct tca aat gtt cct ttc att      960
Leu Asn Glu Ile Ala Gln Ala Leu Asp Ala Ser Asn Val Pro Phe Ile
305                 310                 315                 320 ttt gta ttg agg cct aat gaa gaa acg gcg tcg tgg ttg cca gtt ggt     1008
Phe Val Leu Arg Pro Asn Glu Glu Thr Ala Ser Trp Leu Pro Val Gly
                325                 330                 335 aat tta gag gac aag act aaa aag ggt ttg tac atc aaa ggg tgg gtc     1056
Asn Leu Glu Asp Lys Thr Lys Lys Gly Leu Tyr Ile Lys Gly Trp Val
            340                 345                 350 cca cag ctt acg atc atg gaa cat tca gca aca ggc ggg ttc atg act     1104
Pro Gln Leu Thr Ile Met Glu His Ser Ala Thr Gly Gly Phe Met Thr
        355                 360                 365 cat tgt ggt act aat tcg gtt ctg gaa gcc atc act ttt ggc gtg cca     1152
His Cys Gly Thr Asn Ser Val Leu Glu Ala Ile Thr Phe Gly Val Pro
370                 375                 380 atg ata aca tgg cca ctt tat gct gat caa ttc tac aac gag aag gta     1200
Met Ile Thr Trp Pro Leu Tyr Ala Asp Gln Phe Tyr Asn Glu Lys Val
385                 390                 395                 400 gtc gag gtt agg gga ttg gga atc aaa atc ggg ata gat gta tgg aat     1248
Val Glu Val Arg Gly Leu Gly Ile Lys Ile Gly Ile Asp Val Trp Asn
                405                 410                 415 gaa ggg att gag atc acg ggc cct gta ata gaa agc gcc aag att aga     1296
Glu Gly Ile Glu Ile Thr Gly Pro Val Ile Glu Ser Ala Lys Ile Arg
            420                 425                 430 gaa gca att gag aga cta atg atc agt aat ggt tct gag gaa att ata     1344
Glu Ala Ile Glu Arg Leu Met Ile Ser Asn Gly Ser Glu Glu Ile Ile
        435                 440                 445 aat att agg gat aga gta atg gct atg agc aaa atg gct cag aat gca     1392
Asn Ile Arg Asp Arg Val Met Ala Met Ser Lys Met Ala Gln Asn Ala
450                 455                 460 aca aat gaa ggt gga tct tcg tgg aac aat ctc act gct ctc att caa     1440
Thr Asn Glu Gly Gly Ser Ser Trp Asn Asn Leu Thr Ala Leu Ile Gln
465                 470                 475                 480 cat atc aag aat tat aat ctt aat tag                                 1467
His Ile Lys Asn Tyr Asn Leu Asn
                485

<210> SEQ ID NO 19
<211> LENGTH: 488
<212> TYPE: PRT
<213> ORGANISM: Solanum tuberosum Sgt1

<400> SEQUENCE: 19

Met Val Ala Thr Cys Asn Ser Gly Glu Ile Leu His Val Leu Phe Leu
1               5                   10                  15

Pro Phe Leu Ser Ala Gly His Phe Ile Pro Leu Val Asn Ala Ala Arg
            20                  25                  30

Leu Phe Ala Ser Arg Gly Val Lys Ala Thr Ile Leu Thr Thr Pro His
        35                  40                  45

Asn Ala Leu Leu Phe Arg Ser Thr Ile Asp Asp Val Arg Ile Ser
    50                  55                  60

Gly Phe Pro Ile Ser Ile Val Thr Ile Lys Pro Ser Ala Glu Val
65                  70                  75                  80

Gly Leu Pro Glu Gly Ile Glu Ser Phe Asn Ser Ala Thr Ser Pro Glu
                85                  90                  95

Met Pro His Lys Ile Phe Tyr Ala Leu Ser Leu Leu Gln Lys Pro Met
            100                 105                 110

Glu Asp Lys Ile Arg Glu Leu Arg Pro Asp Cys Ile Phe Ser Asp Met
```

-continued

```
                115                 120                 125
Tyr Phe Pro Trp Thr Val Asp Ile Ala Asp Glu Leu His Ile Pro Arg
    130                 135                 140

Ile Leu Tyr Asn Leu Ser Ala Tyr Met Cys Tyr Ser Ile Met His Asn
145                 150                 155                 160

Leu Lys Val Tyr Arg Pro His Lys Gln Pro Asn Leu Asp Glu Ser Gln
                165                 170                 175

Ser Phe Val Val Pro Gly Leu Pro Asp Glu Ile Lys Phe Lys Leu Ser
                180                 185                 190

Gln Leu Thr Asp Asp Leu Arg Lys Ser Asp Asp Gln Lys Thr Val Phe
            195                 200                 205

Asp Glu Leu Leu Glu Gln Val Glu Asp Ser Glu Glu Arg Ser Tyr Gly
        210                 215                 220

Ile Val His Asp Thr Phe Tyr Glu Leu Glu Pro Ala Tyr Val Asp Tyr
225                 230                 235                 240

Tyr Gln Lys Leu Lys Lys Pro Lys Cys Trp His Phe Gly Pro Leu Ser
                245                 250                 255

His Phe Ala Ser Lys Ile Arg Ser Lys Glu Leu Ile Ser Glu His Asn
                260                 265                 270

Asn Asn Glu Ile Val Ile Asp Trp Leu Asn Ala Gln Lys Pro Lys Ser
            275                 280                 285

Val Leu Tyr Val Ser Phe Gly Ser Met Ala Arg Phe Pro Glu Ser Gln
        290                 295                 300

Leu Asn Glu Ile Ala Gln Ala Leu Asp Ala Ser Asn Val Pro Phe Ile
305                 310                 315                 320

Phe Val Leu Arg Pro Asn Glu Gly Thr Ala Ser Trp Leu Pro Val Gly
                325                 330                 335

Asn Leu Glu Asp Lys Thr Lys Lys Gly Leu Tyr Ile Lys Gly Trp Val
                340                 345                 350

Pro Gln Leu Thr Ile Met Glu His Ser Ala Thr Gly Gly Phe Met Thr
            355                 360                 365

His Cys Gly Thr Asn Ser Val Leu Glu Ala Ile Thr Phe Gly Val Pro
        370                 375                 380

Met Ile Thr Trp Pro Leu Tyr Ala Asp Gln Phe Tyr Asn Glu Lys Val
385                 390                 395                 400

Val Glu Val Arg Gly Leu Gly Ile Lys Ile Gly Ile Asp Val Trp Asn
                405                 410                 415

Glu Gly Ile Glu Ile Thr Gly Pro Val Ile Glu Ser Ala Lys Ile Arg
                420                 425                 430

Glu Ala Ile Glu Arg Leu Met Ile Ser Asn Gly Ser Glu Glu Ile Ile
            435                 440                 445

Asn Ile Arg Asp Arg Val Met Ala Met Ser Lys Met Ala Gln Asn Ala
        450                 455                 460

Thr Asn Glu Gly Gly Ser Ser Trp Asn Asn Leu Thr Ala Leu Ile Gln
465                 470                 475                 480

His Ile Lys Asn Tyr Asn Leu Asn
                485
```